United States Patent [19]

Oertel et al.

[11] 4,223,147
[45] Sep. 16, 1980

[54] METHYLOL DERIVATIVES OF 2,2,6,6-TETRAALKYLPIPERIDINES AND THEIR PRODUCTION

[75] Inventors: Harald Oertel, Odenthal; Paul Uhrhan; Reinhard Lantzsch, both of Cologne; Ernst Roos, Odenthal; Hans Schröer, Dormagen; Dieter Arlt, Cologne, all of Fed. Rep. of Germany

[73] Assignee: Bayer Aktiengesellschaft, Leverkusen, Fed. Rep. of Germany

[21] Appl. No.: 834,763

[22] Filed: Sep. 19, 1977

[30] Foreign Application Priority Data

Sep. 21, 1976 [DE] Fed. Rep. of Germany ...... 2642446

[51] Int. Cl.$^2$ ............................................ C07D 211/58
[52] U.S. Cl. .................................. 546/224; 546/244; 546/16; 546/215; 546/191; 546/196; 546/190; 546/225; 546/227; 546/221; 546/222; 546/223; 546/242; 546/245; 260/45.8 NP
[58] Field of Search ......................... 546/16, 224, 244

[56] References Cited

U.S. PATENT DOCUMENTS 3,684,765    8/1972    Matsui et al. ..................... 546/224

*Primary Examiner*—Henry R. Jiles
*Assistant Examiner*—Robert T. Bond
*Attorney, Agent, or Firm*—Sprung, Felfe, Horn, Lynch & Kramer

[57] ABSTRACT

The invention relates to new methylol derivatives of 2,2,6,6-tetraalkylpiperidines, to their production and to their use as chemically attached stabilizers for polymers containing reactive OH- and NH-groups.

5 Claims, No Drawings

METHYLOL DERIVATIVES OF 2,2,6,6-TETRAALKYLPIPERIDINES AND THEIR PRODUCTION

This invention relates to new methylol derivatives of 2,2,6,6-tetraalkylpiperidines, to their production and to their use as chemically attached stabilisers for polymers containing reactive OH- and NH-groups.

Derivatives of 2,2,6,6-tetraalkylpiperidines are known, some of which have recently proved to be particularly suitable for stabilising polymers. Some representatives of this series have been found to be particularly effective for use in polyurethanes, reducing both the extent to which they are discoloured and also their loss of strength on exposure to light (sunlight or UV-light).

However, it has been found that the stabilisation of the polymers, especially polyurethane elastomer filaments or polyurethane coatings, with derivatives of 2,2,6,6-tetraalkylpiperidines becomes less effective surprisingly quickly, for example when the filaments or coatings are treated with dry cleaning solvents or when they are dyed in (normally) weakly acid dye baths. In addition, dyeing is accompanied by considerable disturbances in dyeing behaviour. For example, only part of the dye is normally attached to the fibre, the rest being kept in solution in the form of a "dry salt" of the basic tetraalkyl piperidine derivative and the acid groups of the dye, or forming a non-abrasion-resistant deposit on the surface of the fibres. When PU-elastomer filaments or elastomer films which, for example, have been extracted with solvents or boiled with acetic acid solutions ("blank dyeing") are exposed to light, the stabilising effect substantially or completely disappears.

However, extraction-resistant stabilisation is required for numerous polymer applications, especially for shaped articles with a large surface area, as is particularly the case with filaments and fibres and also with films, coatings and microporous films (e.g. for artificial leather).

Compounds based on 2,2,6,6-tetraalkyl piperidines have now been found which, on the one hand, have a very high stabilising activity and, on the other hand, contain one or more reactive groups through which they are able to react with the polymers to be stabilised. Stabilised polymers, preferably polyurethane elastomer filaments, films and coatings with a permanent washing-resistant, boiling-resistant, acid-resistant, dry-cleaning-resistant and solvent-resistant stabilisation based on 2,2,6,6-tetraalkyl piperidine light stabilisers are thus obtained.

Accordingly, the present invention provides 2,2,6,6-tetraalkyl piperidine compounds which contain one or more reactive groups corresponding to the formula:

—CO—NH—CH$_2$—OH and/or

—CO—NH—CH$_2$—Oalkyl

More particularly, the invention relates to compounds corresponding to the general formula (I):

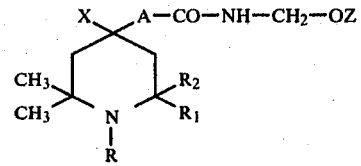

in which

Z represents hydrogen or an alkyl group,

R represents hydrogen, a straight-chain or branched-chain alkyl radical with 1 to 20 carbon atoms, an alkenyl radical with 3 to 5 carbon atoms, an aralkyl radical with 7 to 12 carbon atoms, the group —CH—CHR$_6$—OH where R$_6$ is hydrogen, methyl or phenyl, the group —CH$_2$—CH$_2$—CN, the group —CH$_2$—CH$_2$—COOalkyl or the group —CH$_2$—CH—COOalkyl
      |
     CH$_3$ R$_1$ and R$_2$ which may be the same or different each represents a straight-chain or branched-chain alkyl radical with 1 to 6 carbon atoms or R$_1$ and R$_2$, together with the ring carbon atom to which they are attached, form a cycloalkyl ring with 5 to 7 carbon atoms,

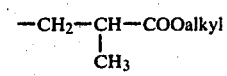

—A— represents

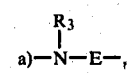

(b) —O—E— or (c) —CO—NH—NH—;

in case (a), X in the general formula I represents hydrogen, in case (b), X represents hydrogen, the cyano group or a —COOR$_7$—Group where R$_7$ is an alkyl radical, preferably a methyl or ethyl radical, and in case (c), X represents the OH-group, and R$_3$ represents hydrogen, a straight-chain or branched-chain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonyl-alkyl radical preferably containing 1 to 3 carbon atoms in the alkoxy moiety, an aryl radical with 6 to 10 carbon atoms, the group —CH$_2$—CH(R$_6$)—OH (where R$_6$ is hydrogen, methyl or phenyl), the group

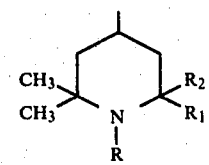

the group

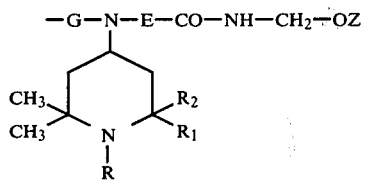

where G is an alkylene group with 2 to 6 carbon atoms, an aralkylene group with 8 to 10 carbon atoms or an arylene group with 6 to 8 carbon atoms, or the group

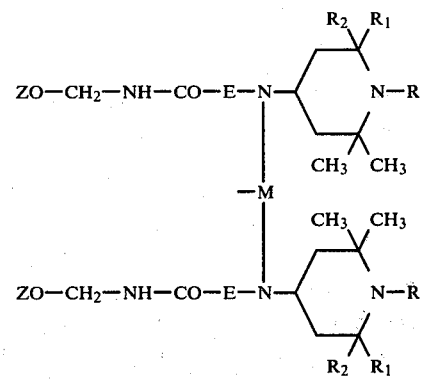

where M is an alkane triyl group with 5 to 6 carbon atoms or an aralkane triyl group with 9 carbon atoms, or the group $-E-CO-NH-CH_2-OZ$, and E represents a $C_1$ to $C_3$ alkylene radical, the group $-CH_2-CH(R_6)-O-$ (where $R_6$ is as defined above), the group $-(CH_2)_3-NH-$, the group $-C_1$ to $C_3$-alkylene$-CO-NH-$, the group $-C_1$ to $C_3$-alkylene$-CO-NH-NH-$ or the group $-CO-NH-NH-$ or a direct bond, the radical $-CO-NH-CH_2-OZ$ never being directly attached twice to the nitrogen atom in formula (a).

Compounds corresponding to any of formulae II, III and IV below have proved to be particularly preferred:

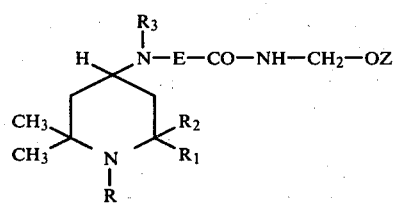

in which Z, E, R, $R_1$, $R_2$ and $R_3$ are as defined above;

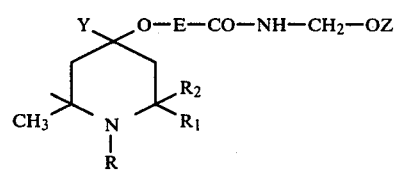

in which

Y represents hydrogen, the cyano group or a $COOR_7$-group, $R_7$ represents a methyl or ethyl radical, and Z, E, R, $R_1$ and $R_2$ are as defined above; and

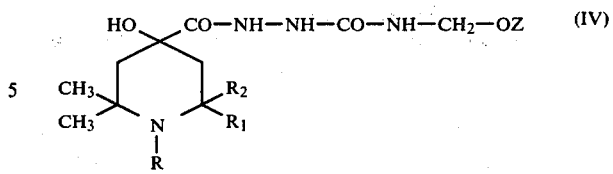

in which Z, R, $R_1$ and $R_2$ are as defined above.

The present invention also provides a process for producing N-alkoxymethyl derivatives of 4-amino-2,2,6,6-tetraalkyl piperidines substituted in the one-position or unsubstituted and corresponding to the general formula (V)

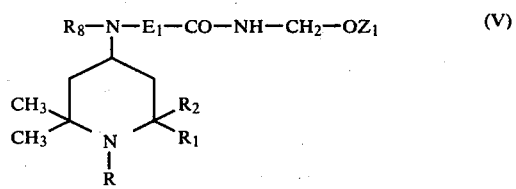

in which

R represents hydrogen, a straight-chain or branched-chain alkyl radical with 1 to 20 carbon atoms, an alkenyl radical with 3 to 5 carbon atoms, an aralkyl radical with 7 to 12 carbon atoms, the group $-CH_2-CHR_6-OH$, where $R_6$ represents hydrogen, methyl or phenyl, the group $-CH_2-CH_2-CN$, the group $-CH_2-CH_2-COOalkyl$ or the group

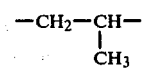

COOalkyl, $R_1$ and $R_2$ may be the same or different and each represents a chain or branched-chain alkyl radical with 1 to 6 carbon atoms or $R_1$ and $R_2$, together with the ring carbon atoms to which they are attached, form a cycloalkyl ring with 5 to 7 carbon atoms, $Z_1$ represents an alkyl group, $R_8$ represents hydrogen, a straight-chain or branched-chain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxy-carbonylethyl radical preferably containing from 1 to 3 carbon atoms in the alkoxy moiety, an aryl radical with 6 to 10 carbon atoms, the group $-CH_2CH(R_6)-OH$ (in which $R_6$ represents hydrogen, methyl or phenyl), the group

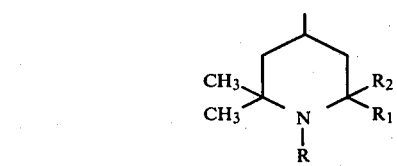

the group $-E_1-CO-NH-CH_2-OZ_1$, the group

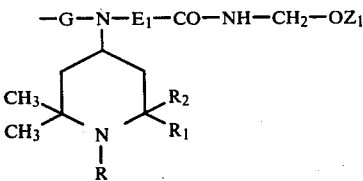

where G is an alkylene group with 2 to 6 carbon atoms, an aralkylene group with 8 to 10 carbon atoms or an arylene group with 6 to 8 carbon atoms, or the group

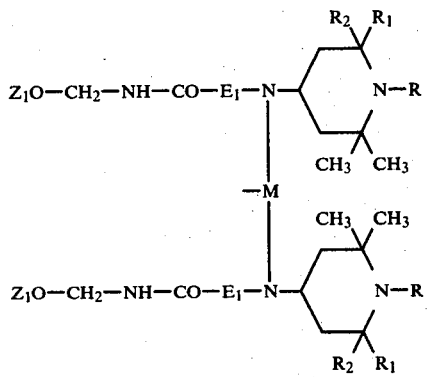

in which M represents an alkane triyl group with 5 to 6 carbon atoms or an aralkane triyl group with 9 carbon atoms, $E_1$ represents a direct bond, the group —$(CH_2)_3NH$—, the group $C_1$ to $C_3$—alkylene—CO—NH—, the group —$C_1$ to $C_3$—alkylene—CO—NH—NH—, the group —CO—NH—NH— or the group —$CH_2$—$CH(R_6)$—O (where $R_6$ represents hydrogen, methyl or phenyl), wherein a compound corresponding to the general formula

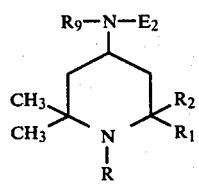

in which

R, $R_1$ and $R_2$ are as defined above, $R_9$ represents hydrogen, a straight-chain or branched-chain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonyl-ethyl radical with 1 to 3 carbon atoms in the alkoxy moiety, an aryl radical with 6 to 10 carbon atoms, the group —$CH_2$—$CH(R_6)$—OH (in which $R_6$ represents hydrogen, methyl or phenyl), the group

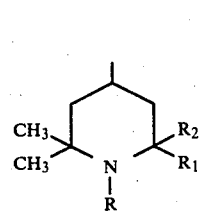

the group

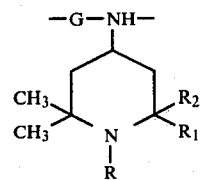

where G is an alkylene group with 2 to 6 carbon atoms, an aralkylene group with 8 to 10 carbon atoms or an arylene group with 6 to 8 carbon atoms, or the group

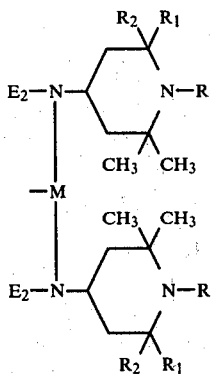

where M is an alkane triyl group with 5 to 6 carbon atoms or an aralkane triyl group with 9 carbon atoms, or the group E, and $E_2$ represents hydrogen, the group —$(CH_2)_3$—$NH_2$, the group $C_1$ to $C_3$-alkylene—CO—$NH_2$, the group $C_1$ to $C_3$—alkylene—CO—NH—$NH_2$, the group —CO—NH—$NH_2$ or the group —$CH_2$—$CH(R_6)$—OH (in which $R_6$ represents hydrogen, methyl or phenyl), is reacted with an alkoxymethyl isocyanate of the formula $Z_1O$—$CH_2NCO$ or with a masked alkoxymethyl isocyanate in such a quantity that one alkoxymethyl isocyanate or masked alkoxymethyl isocyanate is used for every free isocyanatereactive NH- and/or OH-group.

The invention also provides a process for producing N-alkoxymethyl derivatives of 4-amino-2,2,6,6-tetraalkyl piperidines substituted in the one-position or unsubstituted and corresponding to the general formula VI

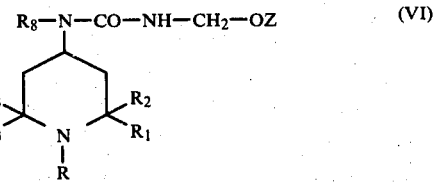 (VI)

in which

Z represents hydrogen or an alkyl group, and

R, $R_1$, $R_2$ and $R_8$ are as defined above, wherein a compound corresponding to the formula

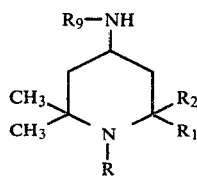

in which

R₉ is as defined above, is reacted initially with cyanic acid and subsequently with formaldehyde whereby each NH-group which is not attached to the ring reacts with the cyanic acid to form an

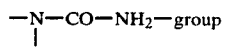

and then an

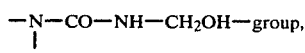

optionally followed by etherification in an acidic medium with an alcohol of the formula ZOH.

The invention also provides a process for producing N-alkoxymethyl derivatives of 4-amino-2,2,6,6-tetraalkyl piperidines substituted in the one-position or unsubstituted and corresponding to the general formula VII,

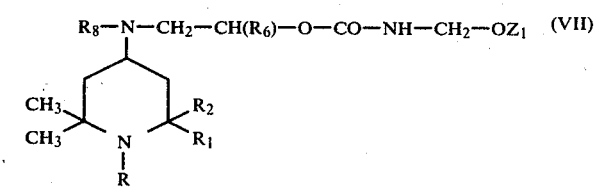

in which

R, R₁, R₂ and Z₁ are as previously defined,

R₆ represents hydrogen, methyl or phenyl,

R₁₀ represents hydrogen, a straight-chain or branched-chain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonylethyl radical with 1 to 3 carbon atoms in the alkoxy moiety, an aryl radical with 6 to 10 carbon atoms, the group —CH₂—CH(R₆)—OH (where R₆ is hydrogen, methyl or phenyl), the group

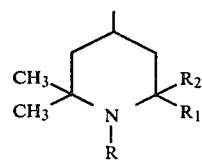

the group

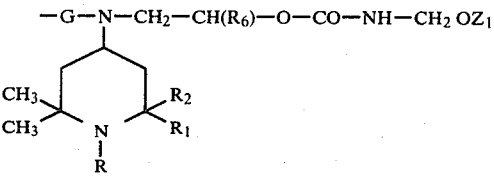

where G is an alkylene group with 2 to 6 carbon atoms, an aralkylene group with 8 to 10 carbon atoms or an arylene group with 6 to 8 carbon atoms, the group

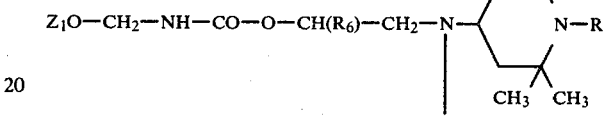

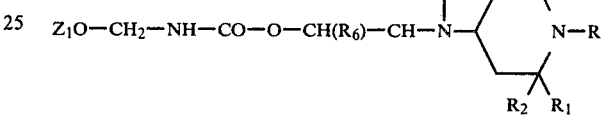

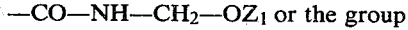
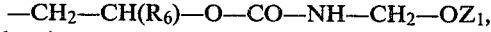

where M is an alkane triyl group with 5 to 6 carbon atoms or an aralkane triyl group with 9 carbon atoms, the group —CO—NH—CH₂—OZ₁ or the group

—CH₂—CH(R₆)—O—CO—NH—CH₂—OZ₁, wherein a compound corresponding to the general formula

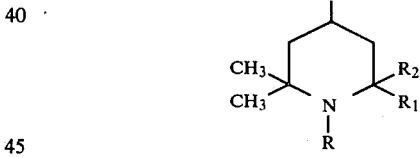

in which

R₉ is as previously defined, is reacted initially with 1 mole of alkylene oxide corresponding to the formula:

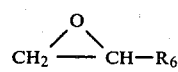

and subsequently with an alkoxymethyl isocyanate of the formula:

whereby each primary or secondary amino group which is not attached to the ring reacts with the alkylene oxide to form an

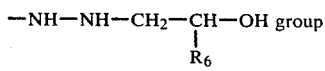

or an

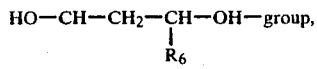

after which the OH- and/or secondary amino groups react with the isocyanate.

The invention also relates to a process for producing N-alkoxymethyl derivatives of 4-amino-2,2,6,6-tetraalkyl piperidines which are unsubstituted or substituted in the oneposition, corresponding to the general formula (VIII):

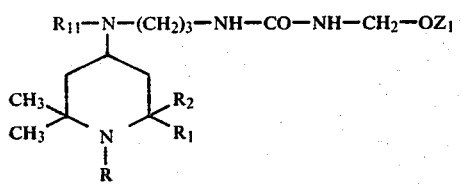

in which

R, $R_1$, $R_2$ and $Z_1$ are as previously defined, and $R_{11}$ represents hydrogen, a straight-chain or branchedchain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonyl-ethyl radical with 1 to 3 carbon atoms in the alkoxy moiety, an aryl radical with 6 to 10 carbon atoms, the group —$CH_2$—$CH(R_6)$-OH (where $R_6$ represents hydrogen, methyl or phenyl), the group

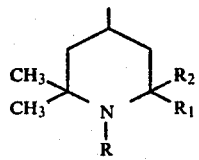

the group

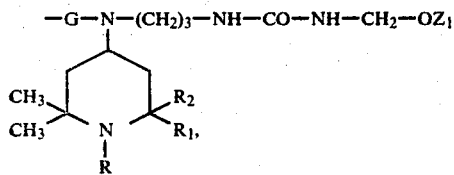

where G is an alkylene group with 2 to 6 carbon atoms, an aralkylene group with 8 to 10 carbon atoms or an arylene group with 6 to 8 carbon atoms, the group

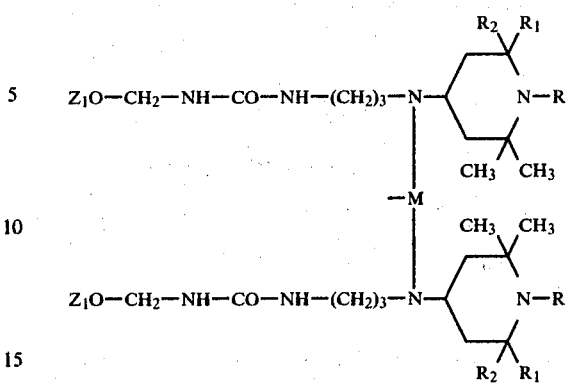

where M represents an alkane triyl group with 5 to 6 carbon atoms or an aralkane triyl group with 9 carbon atoms, the group
—CO—NH—$CH_2$—$OZ_1$ or the group
—$(CH_2)_3$—NH—CO—NH—$CH_2$—$OZ_1$,
wherein a compound corresponding to the general formula

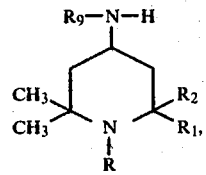

in which $R_9$ is as previously defined, is first cyanoethylated with acrylonitrile on each NH-group which is not attached to the ring, after which the cyanoethyl group is catalytically reduced to form amino groups and the free $NH_2$-groups are then reacted with an alkoxymethyl isocyanate of the formula:

$Z_1O$—$CH_2$—NCO or with a masked alkoxymethyl isocyanate.

The invention also relates to a process for producing N-alkoxymethyl derivatives of 4-amino-2,2,6,6-tetraalkyl piperidines substituted in the one-position or unsubstituted and corresponding to the general formula (IX)

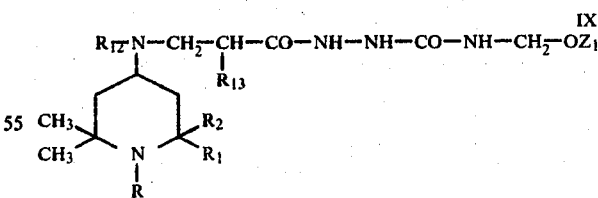

in which

R, $R_1$, $R_2$ and $Z_1$ are as previously defined, and $R_{13}$ represents hydrogen or methyl, $R_{12}$ represents hydrogen, a straight-chain or branchedchain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonyl ethyl radical with 1 to 3 carbon atoms in the alkoxy moiety, an aryl radical with 6 to 10 carbon atoms, the group —CH$_2$—CH(R$_6$)—OH (where R$_6$ represents hydrogen, methyl or phenyl), the group

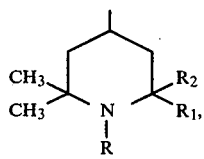

the group

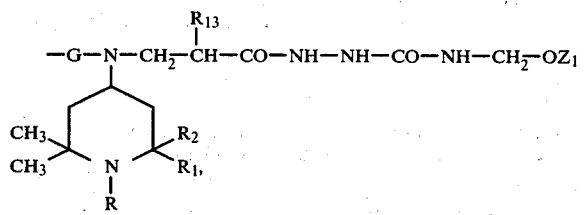

where G represents an alkylene group with 2 to 6 carbon atoms, an aralkylene group with 8 to 10 carbon atoms or an arylene group with 6 to 8 carbon atoms, the group

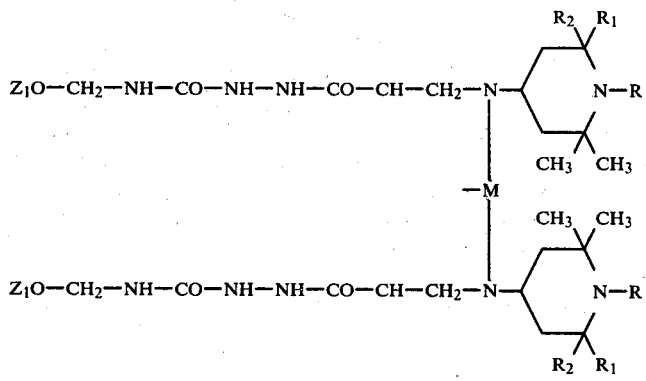

where M represents an alkane triyl group with 5 to 6 carbon atoms or an aralkane triyl group with 9 carbon atoms, the group -CO-NH-CH$_2$-OZ$_1$ or the group

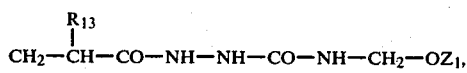

wherein a compound corresponding to the general formula

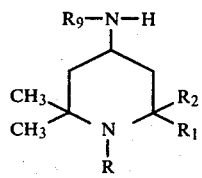

in which

R$_9$ is as previously defined, is reacted initially with acrylic or methacrylic acid alkyl esters on each NH-group which is not attached to the ring to form a group

the ester groups obtained are then reacted with hydrazine hydrate to form carboxylic acid hydrazide and the carboxylic acid hydrazide thus obtained and any still free secondary amino groups are subsequently reacted with an alkoxymethyl isocyanate of the formula

Z$_1$O—CH$_2$—NCO or with a masked alkoxymethyl isocyanate.

The invention also provides a process for producing N-alkoxymethyl derivatives of 4-amino-2,2,6,6-tetraalkyl piperidines which are unsubstituted or substituted in the one-position corresponding to the general formula (X)

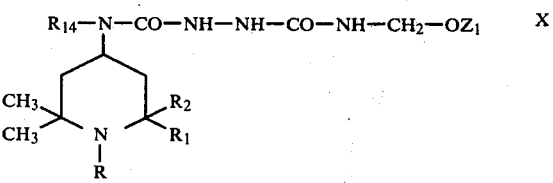   X in which

R, R$_1$, R$_2$ and Z$_1$ are as previously defined, and

R$_{14}$ represents hydrogen, a straight-chain or branchedchain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxycarbonylethyl radical with 1 to 3 carbon atoms in the alkoxy moiety, an aryl radical with 6 to 10 carbon atoms, the group —CH$_2$—CH(R$_6$)—OH (where R$_6$ represents hydrogen, methyl or phenyl), the group

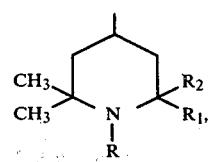

the group

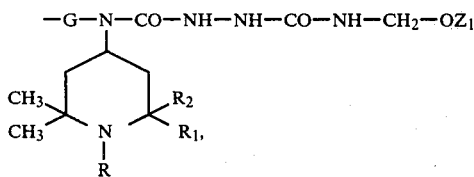

where G is an alkylene group with 2 to 6 carbon atoms, an aralkylene group with 8 to 10 carbon atoms or an arylene group with 6 to 8 carbon atoms, or the group

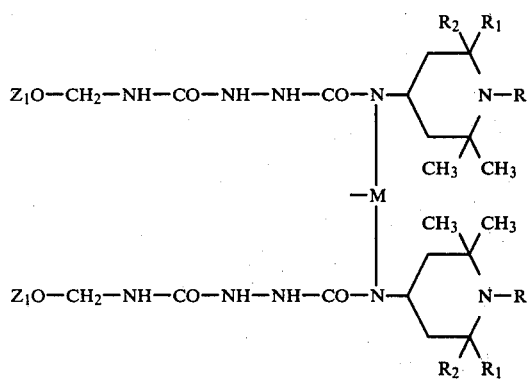

where M is an alkane triyl group with 5 to 6 carbon atoms or an aralkane triyl group with 9 carbon atoms, wherein a compound corresponding to the general formula:

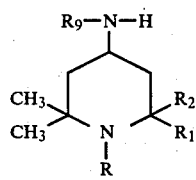

in which $R_9$ has the meaning previously defined, except that $R_9$ may not represent the $\beta$-alkoxy-carbonyl radical, is initially reacted with diphenyl carbonate on each NH-group which is not attached to the ring to form the group —N—CO—OC$_6$H$_5$, the phenyl ester groups obtained are then reacted with hydrazine hydrate to form the group —N—CO—NH—NH$_2$ and this group is in turn reacted with an alkoxymethyl isocyanate corresponding to the formula:

$Z_1O—CH_2—NCO$ or with a masked alkoxymethyl isocyanate.

The invention also relates to a process for producing N-alkoxymethyl derivatives of 4-amino-2,2,6,6-tetraalkyl piperidines which are unsubstituted or substituted in the oneposition and correspond to the general formula XI

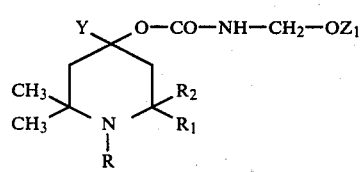

in which

R, $R_1$, $R_2$ and $Z_1$ are as defined above, and

Y represents hydrogen, the cyano group or a COOR$_7$-group where $R_7$ is a $C_1$ to $C_6$-alkyl radical, wherein a compound corresponding to the general formula:

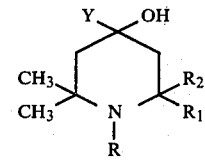

is reacted with an alkoxymethyl isocyanate corresponding to the formula:

$Z_1O—CH_2—NCO$ or with a masked alkoxymethylisocyanate.

The invention also provides a process for producing N-alkoxymethyl derivatives of 4-amino-2,2,6,6-tetraalkyl piperidines which are unsubstituted or substituted in the one-position and corresponding to the general formula XII

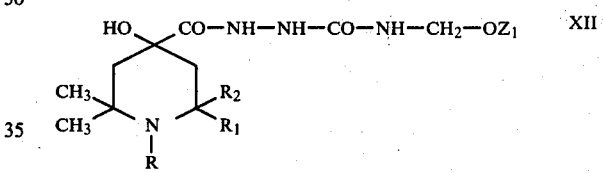

in which

R, $R_1$, $R_2$ and $Z_1$ are as previously defined, wherein a compound corresponding to the general formula:

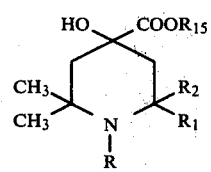

in which $R_{15}$ represents an alkyl group, preferably a methyl or ethyl group, is reacted with hydrazine hydrate to form the corresponding hydrazide and the resulting hydrazide is then reacted with an alkoxymethyl isocyanate of the general formula:

$Z_1O—CH_2—NCO$ or with a masked alkoxymethyl isocyanate.

The invention also relates to the use of N-alkoxymethyl derivatives of 4-amino-2,2,6,6-tetraalkyl piperidines which are unsubstituted or substituted in the one-position and corresponding to the general formula

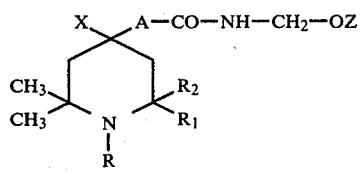   I in which

R, R₁, R₂, X, A and Z are as defined above, for stabilising polymers containing reactive hydrogen attached to O- or N-atoms.

Permanently stabilised polymers containing reactive hydrogen atoms attached to O- or N-atoms in the context of the present invention are characterised by radicals attached to O- or N-atoms said radicals corresponding to the general formula

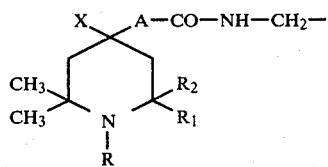

in which

R represents hydrogen, a straight-chain or branched-chain alkyl radical with 1 to 20 carbon atoms, an alkenyl radical with 3 to 5 carbon atoms, an aralkyl radical with 7 to 12 carbon atoms, the group —CH—CHR₆—OH, where R₆ represents hydrogen, methyl or phenyl, the group —CH₂—CH₂—CN, the group —CH₂—CH₂—COOalkyl or the group

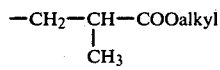

R₁ and R₂ which may be the same or different each represents a straight-chain or branched-chain alkyl radical with 1 to 6 carbon atoms or, R₁ and R₂ together with the ring carbon atom to which they are attached, form a cycloalkyl ring with 5 to 7 carbon atoms, —A—represents

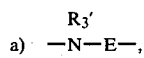

(b) -O-E-or
(c) -CO-NH-NH-;

in case (a), X in general formula I represents hydrogen, in case (b), X represents hydrogen, the cyano group or a —COOR₇-group, where R₇ represents an alkyl radical, preferably a methyl or ethyl radical, and in case (c), X represents the OH-group, and R₃' represents hydrogen, a straight-chain or branched-chain alkyl radical with 1 to 20 carbon atoms, a cycloalkyl radical with 5 to 12 carbon atoms, an aralkyl radical with 7 to 12 carbon atoms, a β-cyanoethyl radical, a β-alkoxy-carbonyl alkyl radical preferably containing from 1 to 3 carbon atoms in the alkoxy moiety, an aryl radical with 6 to 10 carbon atoms, the group —CH₂—CH(R₆)—OH (where R₆ represents hydrogen, methyl or phenyl), the group

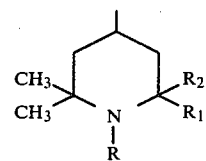

the group

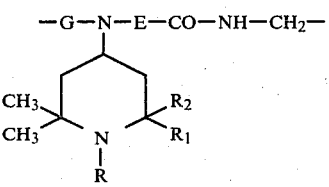

where G is an alkylene group with 2 to 6 carbon atoms, an aralkylene group with 8 to 10 carbon atoms or an arylene group with 6 to 8 carbon atoms, or the group

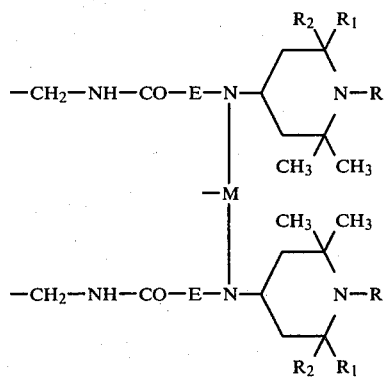

where M is an alkane triyl group with 5 to 6 carbon atoms or an aralkane triyl group with 9 carbon atoms, or the group —E—CO—NH—CH₂—, and E represents a C₁ to C₃-alkylene radical, the group —CH₂—CH(R₆)—O—(where R₆ is as defined above), the group —(CH₂)₃—NH—, the group —C₁ to C₃-alkylene—CO—NH—, the group —C₁ to C₃—alkylene - CO—NH—NH—or a direct bond, the radical —CO—NH—CH₂—never being directly attached twice to the nitrogen atom in formula (a).

In the context of the present invention, permanently stabilised polymers are polymers having a stabilisation which is resistant to extraction by solvents or, for example, aqueous acid solutions by virtue of the chemical attachment of the stabiliser to the polymer.

The stabilised polymers are obtained by adding to the polymers, preferably in solution, from 0.05 to 5% by weight (preferably from 0.1 to 3.0% by weight, and, with particular preference, from 0.1 to 2.0% by weight) of 2,2,6,6-tetraalkyl piperidine compounds containing one or more reactive groups, processing the resulting polymers into shaped articles and reactively attaching the stabilisers to the polymers during or after the shaping stage.

In cases where the stabilisers contain only one reactive group, they may even be attached to the polymers before the shaping stage.

It is of particular advantage that permanently stabilised polymers containing chemically attached stabilisers are obtained without having to alter the structure of the polymers. The type of stabiliser added and the quantity in which it is added may be freely selected virtually up to the forming of shaping stage. The chemical attachment between polymer and stabiliser is preferably initiated during or after the shaping stage or after the production of the polymers, the properties of the polymer remaining virtually unaffected. The stabilising properties, too, are apparently influenced only to a negligible extent, if at all, when the stabilisers are fixed to the polymer. Even very small quantities of stabiliser (for example 0.1 to 0.5% by weight) are able to produce an excellent stabilising effect which is not significantly improved by increasing the amount of stabiliser added to more than 5% by weight, so that extremely rational stabilisation is possible with the stabilisers according to the invention. Even small quantities of the stabilisers according to the invention are able (apparently through a synergistic increase in effect) considerably to improve the stabilising effect with phenolic antioxidants and/or UV-absorbers.

The stabilising effect obtained in accordance with the invention by means of tetraalkyl piperidine stabilisers chemically attached to the polymers enables the 2,2,6,6-tetraalkyl piperidine stabilisers to be used even for relatively critical applications, for example for packaging films in contact with foodstuffs.

Conventional low molecular weight tetraalkyl piperidine stabilisers are readily extracted from polymer films in contact with dilute acids (for example acetic acid and citric acid) or solvents and fats.

According to the invention, any derivatives of 2,2,6,6-tetraalkyl piperidines containing one or more "reactive groups" which are able to react with "reactive sites" of the polymers (i.e. reactive hydrogen on O-, N-heteroatoms), are suitable for use as extraction-resistant stabilisers.

In the context of the invention, polymers with "reactive sites" are polymers containing reactive hydrogen on O- or N-heteroatoms, for example polymers containing hydroxyl, primary and/or secondary amino groups, amide groups, imide groups, urethane groups, urea groups (in which case the —NH—CO—NH—group may even be part of a complicated structure). Suitable polymers are, for example, polyvinyl alcohol or copolymers of vinyl alcohol, polyamides or copolyamides based on lactams, diamines, dicarboxylic acids or aminocarboxylic acids, copolyamides containing proportions of secondary amino groups (incorporation of diethylene triamine or the like), aromatic or heterocyclic copolyamides, gelatin, (co)polymers of (meth)acrylamide, polyhydrazides, polysemicarbazides or polymers containing —CO—NH—NH—, —O—CO—NH—NH—, —NH—CO—NH—NH—groups (optionally as part of complicated structures such as, for example, —NH—CO—NH—NH—CO—NH—), as for example in segmented polyurethane (ureas). The reactive sites of polymers such as these may be present both as part of the chain, as a side chain and also as terminal groups.

In the context of the present invention, "reactive groups" are any groups which are able to react with the reactive sites defined above, but especially methylol groups, methylolether groups, methylol or methylolether groups on N-atoms being particularly preferred.

These particularly preferred methylol or methylolether groups have, for example, the following structural features:

—CO—NH—CH$_2$—OZ
—CO—NH—CO—NH—CH$_2$—OZ
—NH—CO—NH—CO—NH—CH$_2$—OZ but especially —NH—CO—NH—CH$_2$—OZ
—CO—NH—NH—CO—NH—CH$_2$—OZ
—NH—CO—NH—NH—CO—NH—CH$_2$—OZ
—O—CO—NH—NH—CO—NH—CH$_3$—OZ

—O—CO—NH—CH$_2$—OZ in which
Z represents hydrogen or alkyl, preferably $C_1$ to $C_{14}$-alkyl, especially methyl.

Of the preferred formulae II, III and IV compounds mentioned above, compounds containing the following radicals are particularly preferred:
R = hydrogen or methyl;
$R_1$ and $R_2$ = methyl;
Z = methyl;

compounds of formula II:

E = a direct bond;
$R_3$ = hydrogen, a straight-chain or branched-chain $C_1$ to $C_8$-alkyl radical with 1 to 20 carbon atoms, a cyclohexyl radical, a β-cyanoethyl radical, aβ-hydroxyalkyl radical, a (meth)acrylic acid methyl or ethyl ester radical; compounds of formula III:
E = a direct bond;
Y = hydrogen.

The following are examples of the radical R: hydrogen, methyl, ethyl, n-propyl, isopropyl, n-butyl, sec.-butyl, n-hexyl, n-octyl, n-dodecyl, eicosyl, allyl, α-methallyl, benzyl, α-methylbenzyl, p-ethylbenzyl, α-naphthyl methyl, β-hydroxypropyl or β-hydroxy-β-phenylethyl, β-cyanoethyl, β-methoxycarbonyl ethyl and β-ethoxycarbonyl ethyl groups.

Examples of the radicals $R_1$ and $R_2$ include methyl, ethyl, propyl, isopropyl, n-butyl, sec.-butyl and n-hexyl radicals, preferably methyl radicals.

Examples in which $R_1$ and $R_2$ for a cycloalkyl ring with the ring carbon atom to which they are attached include spirocyclopentyl, spirocyclohexyl and spirocycloheptyl rings. $R_1$ and $R_2$ preferably form a spirocyclohexyl ring.

Examples of the radical $R_3$ (E = a direct bond) include H, the methyl, ethyl, n-propyl, isopropyl, n-butyl, sec.-butyl, N-octyl, isooctyl, stearyl, eicosyl, cyclopentyl, cyclohexyl, methyl cyclohexyl, cyclododecyl, benzyl, phenylethyl, β-naphthylmethyl, β-cyanoethyl, 2-methoxycarbonylethyl, 2-ethoxycarbonylethyl, 2-isopropoxy carbonylethyl, phenyl, naphthyl, β-hydroxyethyl, β-hydroxy-β-methylethyl and the β-hydroxy-β-phenylethyl group.

$R_3$ preferably represents hydrogen, $C_1$-$C_8$-alkyl radicals, such as methylethyl, n-propyl, isopropyl, n-butyl, sec.butyl, octyl; also cyclohexyl, methyl cyclohexyl, benzyl, β-cyanoethyl, 2-methoxycarbonylethyl, 2-ethoxycarbonylethyl and β-hydroxyethyl. Hydrogen, methyl, cyclohexyl, benzyl, β-cyanoethyl, 2-ethoxycarbonylethyl and β-hydroxyethyl are particularly preferred meanings for $R_3$.

Further examples of the radical $R_3$ may be represented by the following formulae (E≠a direct bond): —CO—NH—CH$_2$—OH, —CO—NH—CH$_2$—OCH$_3$, —CO—NH—CH$_2$—OC$_3$H$_8$—CH$_2$—CH$_2$—CO—NH—CH$_2$—OH, —CH$_2$—CO—NH—CH$_2$—OCH$_3$, —(CH$_2$)$_3$—CO—NH—CH$_2$—OC$_4$H$_9$, —CH$_2$—CH$_2$—O—CO—NH—CH$_2$—OCH$_3$, —CH$_2$—CH$_2$—O—CO—NH—CH$_2$—OC$_2$H$_5$, —CH$_2$—CH(CH$_3$)—O—CO—NH—CH$_2$—OC$_4$H$_9$, —CH$_2$—CH—C$_6$H$_5$—O—CO—NH—CH$_2$—OCH$_3$, —(CH$_2$)$_3$NH—CO—NH—CH$_2$—OH, —(CH$_2$)$_3$—NH—CO—NH—CH$_2$OCH$_3$——(CH$_2$)$_3$—NH—CO—NH—CH$_2$OC$_3$H$_7$, —CH$_2$—CH$_2$—CO—NH—CO—NH—CH$_2$—OCH$_3$, —CH$_2$—CH$_2$—CO—NH—NH—CO—NH—CH$_2$—OCH$_3$, —CH$_2$—CH$_2$—CO—NH—NH—CO—NH—CH$_2$—OC$_2$H$_5$, —CH$_2$—CH$_2$—CO—NH—NH—CO—NH—CH$_2$—OC$_4$H$_9$, —CO—NH—NH—CO—NH—CH$_2$—OCH$_3$—, —CO—NH—NH—CO—NH—CH$_2$—OC$_3$H$_7$; of these, the —CO—NH—CH$_2$—OZ, the —(CH$_2$)$_3$—NH—CO—NH—CH$_2$—OZ and the (CH$_2$)$_2$—CO—NH—NH—CO—NH—CH$_2$—OZ—radical are preferred, the —CO—NH—CH$_2$—OCH$_3$—radical being particularly preferred.

Examples of the radical G are the ethylene, propylene, tetramethylene or hexamethylene group and also the p-xylylene, p-phenylene or 2,4-tolylene group.

The radical M may be for example one of the following groups:

$$-CH_2-\underset{\underset{CH_2}{|}}{\overset{\overset{CH_3}{|}}{C}}-CH_2-, \quad -CH_2-\underset{\underset{CH_2}{|}}{\overset{\overset{C_2H_5}{|}}{C}}-CH_2-,$$

[1,3-disubstituted benzene ring with —CH$_2$— groups] or [1,2,4-trisubstituted benzene ring with —CH$_2$— groups]

The compounds of general formula II (with an N-function in the 4-position of the piperidine radical) are particularly preferred and effective. The following are examples of particularly preferred compounds in the context of the invention, although the invention is by no means limited to these compounds:

[2,2,6,6-tetramethylpiperidine, H—N]

—NH—CO—NH—CH$_2$OH
—NH—CO—NH—CH$_2$—OCH$_3$
—NH—CO—NH—CH$_2$—OC$_2$H$_5$
—NH—CO—NH—CH$_2$—OC$_4$H$_9$

—N(CH$_3$)—CO—NH—CH$_2$OH

—N(CH$_3$)—CO—NH—CH$_2$—OCH$_3$

—N(iso. C$_3$H$_7$)—CO—NH—CH$_2$—OCH$_3$

—N(sec. C$_4$H$_9$)—CO—NH—CH$_2$—OCH$_3$

—N(cyclohexyl)—CO—NH—CH$_2$—OCH$_3$

[2,2,6,6-tetramethylpiperidine, H—N]

—N(C$_6$H$_{13}$)—CO—NH—CH$_2$—OCH$_3$

—N(C$_{12}$H$_{25}$)—CO—NH—CH$_2$—OCH$_3$

—N(CHCH$_3$—CH$_2$—CH(CH$_3$)$_2$)—CO—NH—CH$_2$—OCH$_3$

—N(CH$_2$—C$_6$H$_5$)—CO—NH—CH$_2$—OCH$_3$

—N(CH$_2$—CH$_2$—CN)—CO—NH—CH$_2$—OCH$_3$

—N(CH$_2$—CH$_2$—CO$_2$—C$_2$H$_5$)—CO—NH—CH$_2$—OCH$_3$

-continued
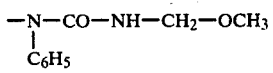
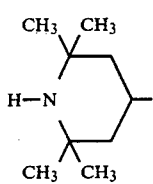
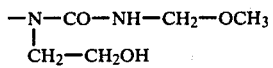
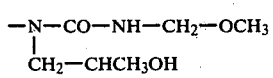
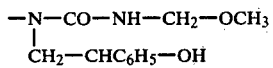
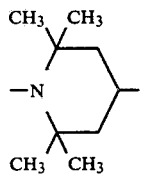
NH—CO—NH—CH₂OH
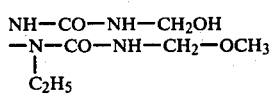
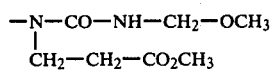
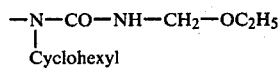
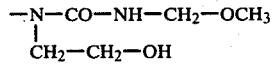
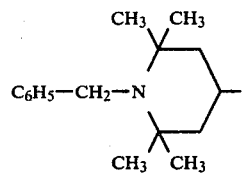
NH—CO—NH—CH₂OCH₃
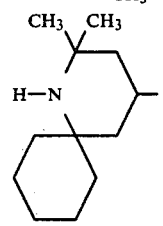
NH—CO—NH—CH₂OH
—NH—CO—NH—CH₂—OCH₃
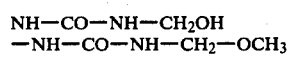
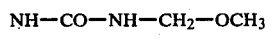
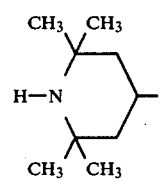
NH—CH₂—CO—NH—CH₂OH
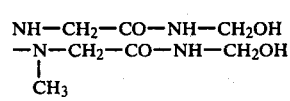
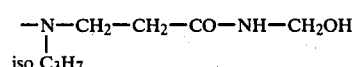
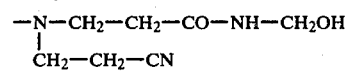
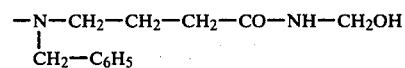
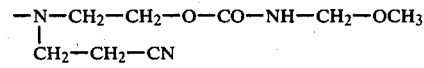

-continued
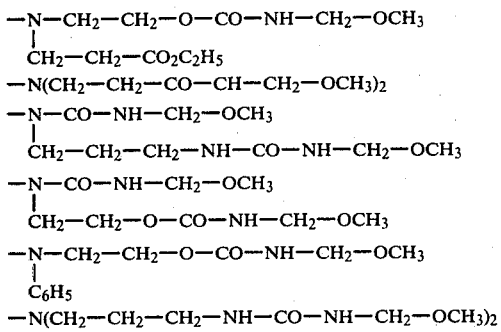
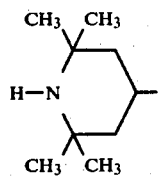
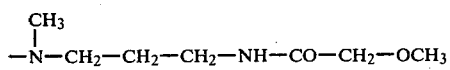
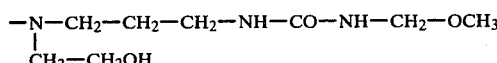
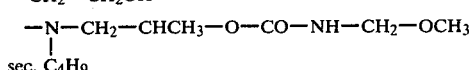
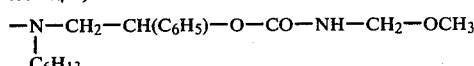
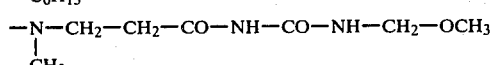
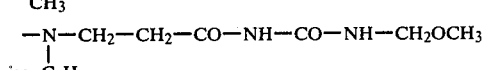
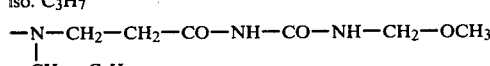
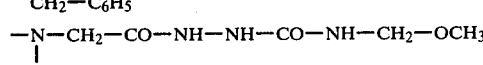
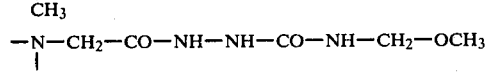
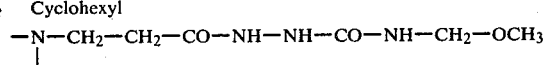
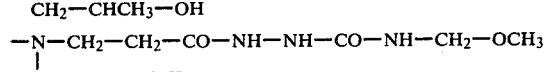
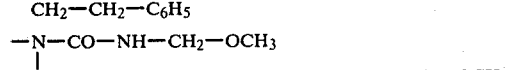
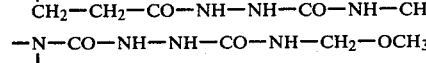
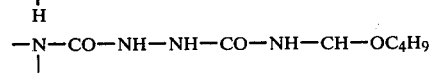
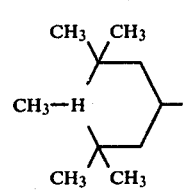
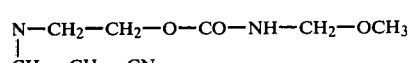
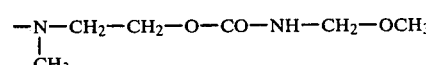
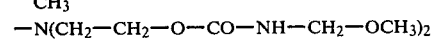
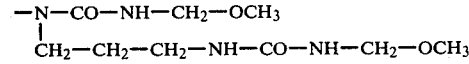

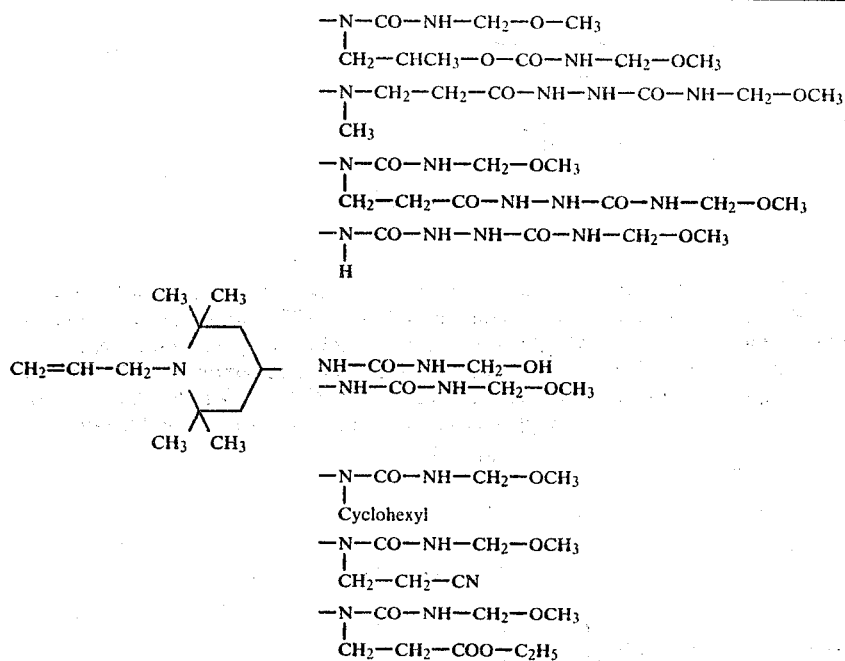

0-(2,2,6,6-tetramethylpiperidin-4-yl)-N-methoxymethylurethane;

0-(1,2,2,6,6-pentamethylpiperidin-4-yl)-N-methoxymethyl urethane;

0-(1-benzyl-2,2,6,6-tetramethylpiperidin-4-yl)-N-methoxymethyl urethane;

0-(2,2,6,6-tetramethyl-4-cyanopiperidin-4-yl)-N-methoxymethyl urethane;

2,2,6,6-tetramethyl-4-hydroxypiperidine-4-carbonyl methoxymethyl semicarbazide;

1,2,2,6,6-pentamethyl-4-hydroxypiperidine-4-carbonyl methoxymethyl semicarbazide;

2,2,6,6-tetramethyl-4-hydroxypiperidine-4-carbonyl butoxymethyl semicarbazide;

N,N'-bis-2,2,6,6-tetramethylpiperidin-4-yl-N,N'-bis-methoxymethylcarbamoyl ethylene diamine;

N,N'-bis-1-benzyl-2,2,6,6-tetramethylpiperdin-4-yl-N,N'bis-methoxymethyl carbamoyl ethylene diamine;

N,N'-bis-1,2,2,6,6-pentamethylpiperidin-4-yl-N,N'-bis-methoxymethyl carbamoyl tetramethylene diamine;

N,N'-bis-1-β-hydroxyethyl-2,2,6,6-tetramethylpiperidin-4-yl-N,N'- bis-methoxymethyl carbamoyl hexamethylene diamine;

N,N'-bis-2,2,6,6-tetramethylpiperidin-4-yl-N,N'-bis-methoxymethyl carbamoyl-p-xylylene diamine;

N,N'-bis-2,2,6,6-tetramethylpiperidin-4-yl-N,N'-bis-ethoxymethyl carbamoyl-p-phenylene diamine;

N,N',N''-tris-2,2,6,6-tetramethylpiperidin-B 4-yl-N,N',N''-tris-methoxymethyl carbamoyl trimethylene ethyl triamine; and N,N',N''-tris-2,2,6,6-tetramethylpiperidin-4-yl-N,N',N''-tris-methoxymethyl carbamoyl trimethylene propyl triamine.

The compounds according to the invention containing "reactive groups" are obtained by the processes previously described. The reaction equations shown by way of example in the following are only intended to serve as illustrations:

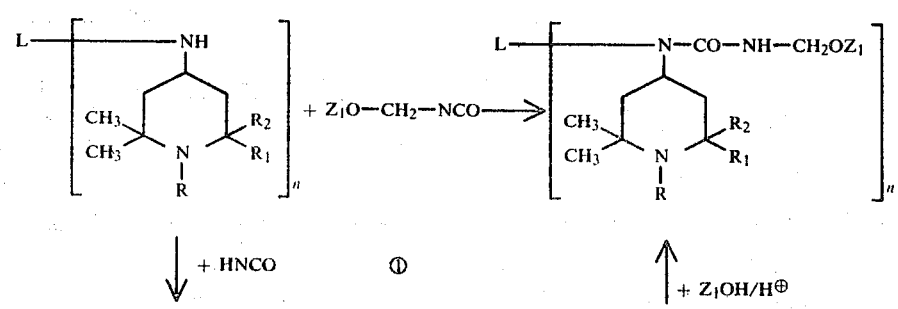

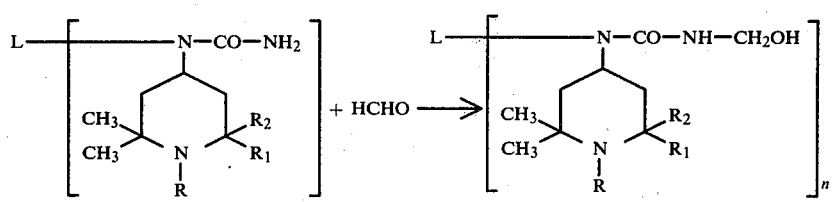

(In this formula scheme and also in the following formula schemes, L may represent, for example, hydrogen or a monofunctional or polyfunctional radical).

The production of the 4-aminopiperidines required as starting materials is described, for example, in German Offenlegungsschrift No. 2,349,962.

Both here and in the following, the free alkoxymethyl isocyanate $Z_1O-CH_2-NCO$ may also be replaced by a "masked" alkoxymethyl isocyanate, for example, an alkoxyaceto-nitrile carbonate. Under the reaction conditions, the latter evolves $CO_2$ to form the alkoxymethyl isocyanate which immediately reacts further with the aminopiperidine.

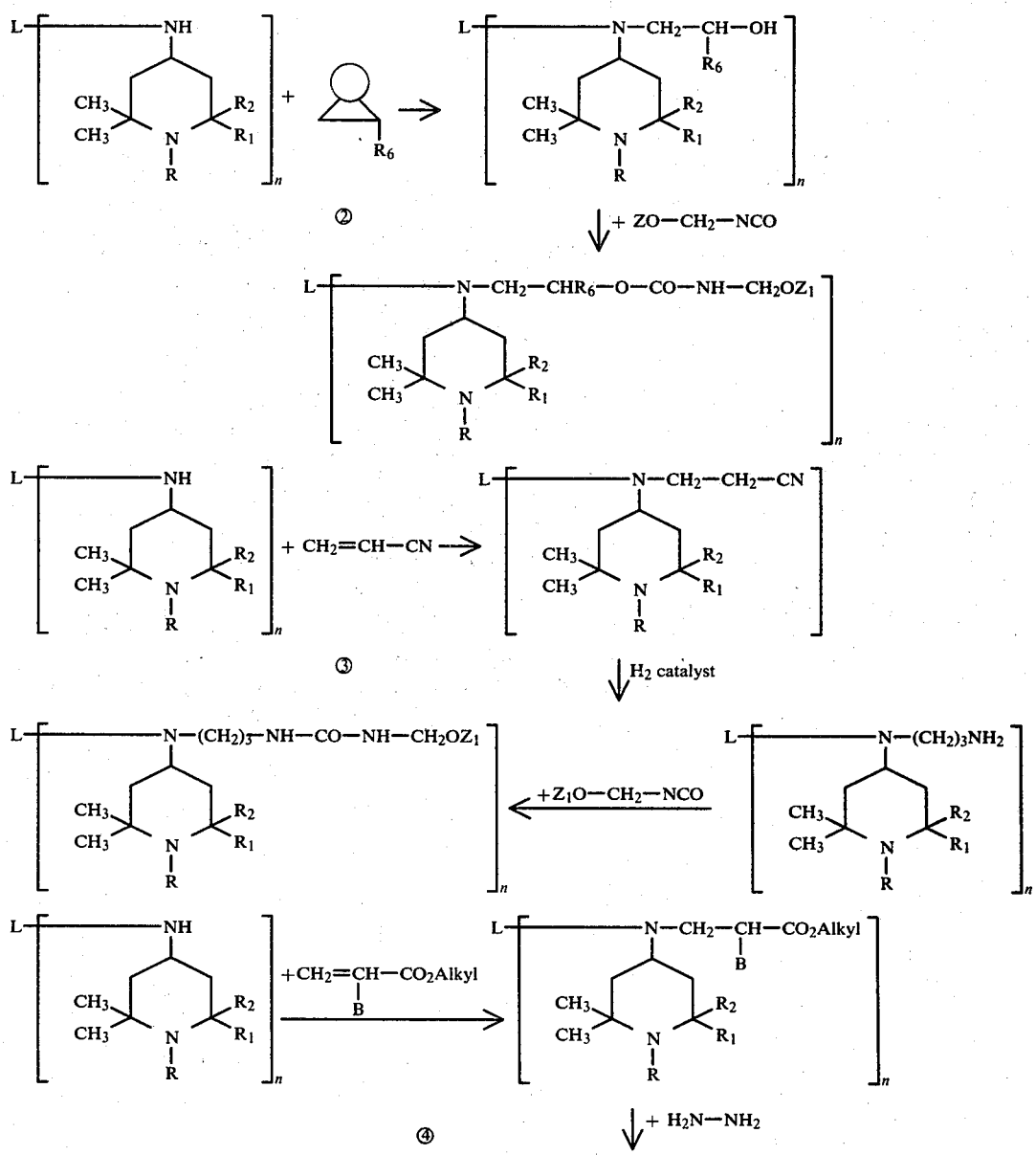

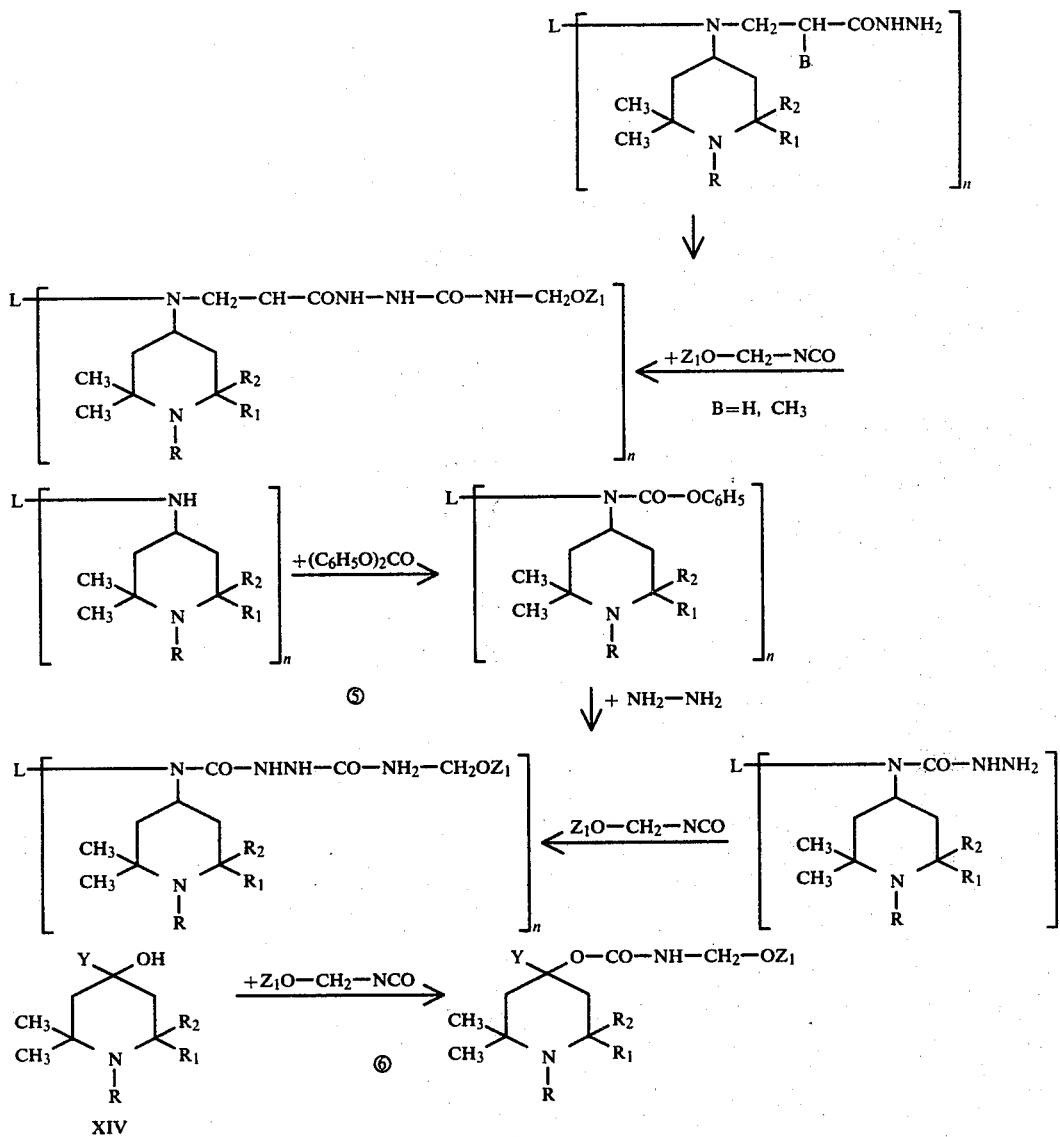
The 4-hydroxypiperidines of general formula XIV required as starting materials for reaction (6) are described inter alia in German Offenlegungschrift No. 2,352,658 (Y=H) and in German Offenlegungsschrift No. 1,695,738 (Y=CN).
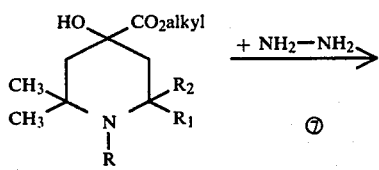
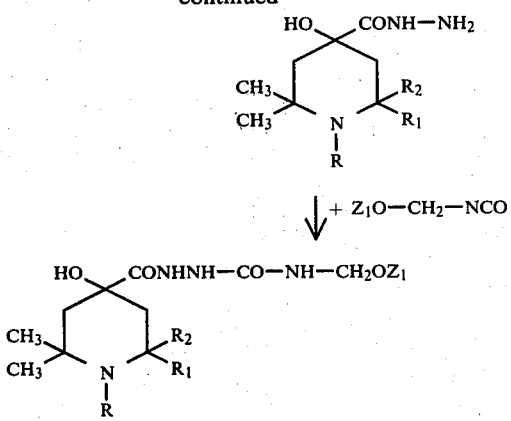
In cases where the reactive group is repeatedly introduced into the molecule of the compounds according to the invention, for example in compounds such as

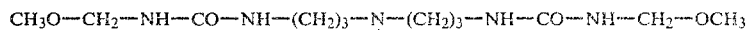
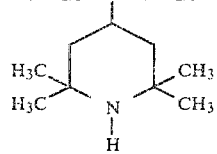

or

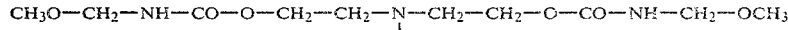
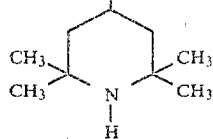

they are able to react monofunctionally or even bifunctionally with "reactive sites" of the polymers; in the latter case, they additionally have a crosslinking function.

A crosslinking effect such as this is highly desirable in certain cases (for example in polyurethane coatings or finishes based on isophorone diisocyanate which are soluble in so-called soft solvents), because, in addition to the stable lightproofing effect, better substrate anchorage and resistance to aqueous alcohol can be obtained in this way.

Among the tetraalkyl piperidine derivatives, the tetramethyl piperidine-N-methylolmethyl ethers of formula II are particularly preferred because they show particularly high activity and may readily be synthesised. This applies in particular to compounds of formula II in which $R_3$ represents H and E represents a direct bond.

The compounds according to the invention are basically suitable for use as additives for stabilising synthetic polymers, suitable polymers being any of the polymers which have already been proposed for stabilisation by derivatives of tetramethyl piperidine (cf. for example German Auslegeschrift No. 2,349,962 or German Patent Application No. P 25 45 646.6).

One particularly important group of polymers with "reactive sites" to be stabilised are linear or branched polyurethanes which may optionally be present in foamed form and which may be produced by methods known per se from the known starting materials. The polyurethanes are generally obtained by reacting relatively high molecular weight polyhydroxyl compounds (for example polyesters or polyethers with a molecular weight of from about 500 to 5000 and with melting points preferably below 60° C.) with aliphatic, araliphatic or aromatic polyisocyanates (preferably aromatic diisocyanates, such as tolylene diisocyanate or diphenyl methane4,4'-diisocyanate) in the presence of so-called chain extenders or "crosslinkers", i.e. low molecular weight compounds (molecular weight for example from 18 to 400) containing two or more isocyanate-reactive groups (for example water, low molecular weight diols, diamines, hydrazine, dihydrazides or similar compounds, for example, aminoalcohols, aminohydrazides, hydroxy hydrazides, aminosemicarbazides, semicarbazide hydrazide, semicarbazide carbazinic esters, polyols, polyamines or corresponding mixtures of these chain extenders) in one or several stages in the melt or in solvents by a number of known and modifiable processes.

The following are mentioned as examples of suitable starting materials: polyesters of adipic acid and dialcohols with 2 to about 10 carbon atoms, preferably those with more than 5 carbon atoms, the dialcohols optionally being used in admixture to lower the melting points of the polyesters; polyesters of caprolactone and dialcohols, also polalkylene ether diols, especially polytetramethylene ether diols, polytrimethyl ether diols, polypropylene glycol or corresponding copolyethers. Preferred diisocyanates are aromatic diisocyanates, such as diphenyl methane-4,4'-diisocyanate, tolylene diisocyanate, araliphatic diisocyanates, such as m-xylylene diisocyanate, or even aliphatic diisocyanates, such as hexamethylene diisocyanate and dicyclohexyl methane-4,4'-diisocyanate. These starting materials are reacted, optionally with additionally used dialcohols, to form NCO-preadducts which preferably have the structures defined in German Patent Specification No. 734,194. Suitable chain extenders, which may optionally be used in admixture or reacted in stages, are water and/or dialcohols or trialcohols, such as butane diol and p-xylylene glycols, trimethylol propane, aminoalcohols such as ethanol-amine, diamines such as diphenyl methane-4,4'-diamine, 3,3'-dichlorodiphenyl methane-4,4'-diamine, but preferably aliphatic diamines, such as ethylene diamine, 1,2-propylene diamine, isophorone diamine, meta-xylylene diamine and also hydrazine or dihydrazides, such as carbodihydrazide, oxalic acid dihydrazide, glutaric acid dihydrazide, pimellic acid dihydrazide, terephthalic acid dihydrazide, β-alanyl hydrazide or semicarbazide hydrazide, such as β-semicarbazide alanyl hydrazide, optionally in the form of mixtures of the chain extenders.

The compounds according to the invention are preferably used for stabilising segmented polyurethane elastomers which, in addition to urethane groups, also contain NH—CO—NH—groups formed by reaction of isocyanate groups with water and/or compounds containing terminal $NH_2$-groups (for example diamines, dihydrazides, carbodihydrazide, semicarbazide hydrazides or hydrazine) and which have a substantially linear, segmented molecular structure, are soluble before shaping in highly polar solvents, such as dimethyl formamide or dimethyl acetamide, and of which the characteristic segments may be characterised by the following formula moiety:

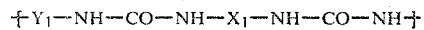

this segment optionally having been formed from the reaction of an NCO-preadduct $OCN-Y_1-NCO$ with a chain extender $H_2N-X_1-NH_2$.

The radical $-Y_1-$ of the NCO-preadduct may have the following composition for example:

$$-R_{20}-NH-CO-O-D-O-CO-NH-R_{20}-$$

or any other usual composition (cf. Belgian Patent Specification No. 734,194).

In the above formula, $R_{20}$ represents a difunctional aliphatic, araliphatic or aromatic radical (of a diisocyanate), D represents the radical of a relatively high molecular weight polyhydroxyl compound with a molecular weight of from 500 to 5000 and with melting points below 60° C. without its terminal hydroxyl groups (for example radical of a polyalkylene ether, polyester, polyacetal, poly-N-alkyl urethane). $X_1$ is the radical of a difunctional chain extender with terminal $NH_2$-groups without the terminal $NH_2$-groups, for example an aliphatic, araliphatic, aromatic or heterocyclic radical, an $-HN-CO-$alkylene$-CO-NH-$radical, an $-NH-CO-NH-(CH_2)_2-CO-NH-$radical or a bond between two N-atoms. The synthesis of polyurethane (ureas) such as these is described in detail, for example in German Auslegeschrift No. 1,270,276 and in Belgian Patent Specification No. 734,194. Polyurethane foams may be produced for example with addition of the stabilisers to the starting components (for example polyethers or polyesters) by known methods and recipes (cf. for example Kunststoff-Handbuch, Vol. VII, Polyurethanes, Carl Hanser Verlag, Munich, 1966, pages 440 to 457, 504, to 531), as may corresponding elastomers, whether of the crosslinked type (for example Vulkollan ®, a product of Bayer AG) or with a substantially linear, segmented structure (for example Desmopan ®-types, products of Bayer AG).

In addition to the compounds according to the invention as stabilisers, other known additives may be worked into the polymer. Additives such as these are, for example, antioxidants of the sterically hindered phenol type, e.g. 2,6-di-tert.-butyl-p-cresol; 4,4'-thio-bis-(6-tert.-butyl-3-methyl phenol); 2,2'-thio-bis-(6-tert.-butyl-4-methyl phenol); $\alpha,\alpha'$-bis-(2-hydroxy-3,5'-dialkyl phenyl)-m-diisopropyl benzenes; 2,2'-methylene-bis-(4-methyl-5-tert.-butyl phenol); 2,2'-methylene-bis-(4-methyl-6-cyclohexyl phenol); 1,1,3-tris-(5-tert.-butyl-4-hydroxy-2-methyl phenyl)-butane; tetrakis-(3,5-di-tert.-butyl-4-hydroxyphenyl propionyl oxymethyl)-methane, also compounds of divalent sulphur, e.g. dilauryl thiodipropionate; compounds of trivalent phosphorus, e.g. triphenyl phosphite, tris-(p-nonyl phenyl)-phosphite and also UV-absorbers based on 2-(2'-hydroxyphenyl)-benzotriazole, such as for example 2-(2'-hydroxy-5'-methyl phenyl)-benzo-triazole, 2-(3',5'-di-tert.-butyl-2'-hyroxyphenyl)-5-chloro-benzotriazole; or benzophenone-based UV-absorbers, e.g. 2-hydroxy-4-octoxybenzophenone; 2',4'-di-tert.-butyl phenyl-3,5-di-tert.-butyl-4-hydroxy benzoate; cyanoacrylic acid esters e.g. $\alpha$-cyano-$\beta$-methanyl-$\beta$-(p-methoxyphenyl)-acrylate and other light stabilisers e.g. nickel 2,2'-thio-bis-(4-tert.-oxtyl phenolate)-n-butylamine. Further representatives are defined in German Auslegeschrift No. 2,349,962, columns 17 to 20. Polymers or copolymers of N,N-dialkylaminoethyl-(meth)-acrylates may also be used for improving dyeability and fastness to chlorine. Two or more of the attachable "TAP" stabilisers (TAP=-tetraalkyl piperidine) according to the invention may also be simultaneously used as stabilisers.

In some cases, it is possible to observe stabilising effects which are clearly attributable to a synergistic increase in effect.

The compounds according to the invention are also effective as polymerisation inhibitors in a number of monomers.

The "reactive" lightproofing agents (stabilisers) according to the invention may readily be incorporated in the polymers by any of the standard processed for compounding additives. For example, the stabiliser may be mixed with the synthetic polymers, preferably in the form of polymer solutions, polymer dispersion/suspensions or emulsions. In most cases, mixing is preferably carried out under such conditions that there is very little reaction, if any, with the reactive groups, especially in the case of stabilisers containing two or more reactive groups which may also have a crosslinking effect. The stabilisers may be added in solid form, in liquid (molten) form or in the form of solutions suspensions or emulsions. In the case of filaments, the stabiliser may be applied in the form of a stabiliser-containing preparation melt. In the case of wet spinning, the stabiliser may be incorporated into the gel filaments from stabiliser-containing coagulation baths. It is preferred to add the stabilisers to solutions of the polymers from which the polymers are shaped.

The quantity of stabiliser used in accordance with the invention is governed by the type and special use of the polymer to be stabilised and may be selected at the discretion of the average expert. Thus, the stabiliser may be added in quantities of from about 0.01 to 5% by weight, preferably in quantities of from 0.1 to 3.0% by weight and, with particular preference, in quantities of from 0.1 to 2.0% by weight, based in each case on the total weight of the stabilised polymer. It is advantageous to add the stabilisers according to the invention in the relatively small quantity which in itself produces an excellent, permanent effect despite the small amounts attached. Thus, additions of less than 0.5% are generally effective, whereas with conventional phenolic stabilisers, for example, considerably larger quantities (1.5 to 2%) are generally required in order to obtain adequate stabilisation.

The reactive attachment of the reactive stabilisers to the polymers is preferably initiated during processing to form the shaped article or in the shaped article itself. The reaction is initiated by treatment at elevated temperatures, generally at temperatures of from about 70° to 200° C., the reaction optionally being accelerated by catalysts. Catalysts suitable for this purpose are acid catalysts, such as ammonium chloride or citric acid. The reactive stabilisers show hardly any volatility or, at least, considerably reduced voltatility at the high temperatures prevailing in the dry spinning duct and, for this reason, are also superior to stabilisers of the additive type.

The reaction temperature and reaction time are so selected that they lead to the required reaction, depending upon the reactive group and upon the reactive site in the polymer. The reaction time may be relatively long, for example about 1 hour in cases where films are dried at around 100° C., although it may be reduced to the order of seconds at correspondingly elevated temperatures, for example in cases where filaments are spun in a highly heated duct (air temperature for example from 200° to 350° C.) or in cases where the filaments are aftertreated, for example on heating godets, in which case the godet temperatures may be in the range from about 140° C. to 350° C.

In special cases (e.g. where there is only one reactive group in the light stabiliser), it is also possible to react the reactive groups in the stabilisers in solution with the polymers and only then to carry out the shaping operation. However, the polymers may also be modified by sprinkling them with the stabilisers, followed by sintering.

However, a particularly suitable and preferred form of carrying out the process according to the invention is to add the reactive stabilisers to solutions of the polymers and to process the solutions into films, coatings or filaments accompanied or followed by reaction of the stabilisers with the shaped articles. One typical example is the spinning of stabiliser-containing polyurethane elastomer solutions with evaporation of the solvents (for example dimethyl formamide) in a hot spinning duct. In cases where the stabiliser according to following example 1 is used together with a small quantity of cataylst, the reaction between the stabiliser and the segmented polyurethane (urea) actually progresses to a large extent by the time the spun filaments leave the spinning duct and is completed by heating the filaments in fixing cabinets, on heating godets or during the heat-fixing of fabrics (for example tenter frame fixing at 190° to 200° C./20 to 60 seconds.

It is particularly preferred to use the reactive stabilisers in shaped articles having a relatively large surface, more especially fibres and filaments, films and coatings or artificial leather structures. In this case, the advantages afforded by the invention for example resistance to extraction, physiologically compatible fixing to the polymer, stability to boiling, dyeing, washing and dry cleaning, develop their full effect. The process according to the invention is particularly valuable for stabilising segmented polyurethanes, especially in the form of the polyurethane elastomer filaments. These advantages of the invention have already been described and are substantiated in detail and compared with the prior art in the following Examples.

The polyurethane solutions are generally knife-coated onto glass plates in the form of approximately 20% solutions in a layer thickness of from about 0.6 to 0.8 mm and then dried in a drying cabinet (for about 30 minutes at 70° L C. + another 40 minutes at 100° C.). Following the application of a little talcum, the films are drawn off.

The films are exposed to light either in the form of approximately 1 cm wide strips and/or in the form of cut filaments. To produce the cut filaments, the films are sliced into filaments with a denier of about 300 dtex in a film-slicing machine equipped with a set of blades.

The solutions may be wet-spun in aqueous coagulation baths (for test purposes through a 20/0.12 mm nozzle into an 80/20 water/DMF bath at 80° C., take-off rate 10 m/minute) and are dried after passing through washing baths. For dry spinning, the slightly heated solution (to approximately 60° C.) is spun through nozzles into a heated spinning duct, to which hot air is additionally delivered in parallel current, and run off at about 100 to 450 m/minute. For test purposes, the filaments are spun through 16/0.2 mm nozzles, run off from the spinning duct at 100 m/minute and, after preparation with talcum, are wound into package form at 130 m/minute. The packages are heated for 1 hour at 130° C.

For Fadeometer testing, the strips of film or filaments are exposed to light on cardboard supports in the Fadeometer. The particular test groups according to the Examples are simultaneously introduced into the exposure chamber so that, even with fluctuations in exposure, comparable light intensities act on the test specimens.

The extraction treatments are carried out in the manner described on films and spun filaments in the form of light packages on small frames. Drying is carried out at room temperature or in a water jet vacuum at 50° C.

$\eta_i$-value: The molecular weight is characterised by the $\eta_i$-value. To this end, 1 g of polymer (expressed as pigment-free polymer) is dissolved while shaking in 100 ml of hexamethyl phosphoramide (HMPA) at room temperature, the solution is filtered through a coarse glass frit and the relative solution viscosities are measured in an Ubbelohde viscosimeter at 25° C.

$\eta_i = (\ln \eta_R)/C$ $\eta_R$ = relative solution viscosity, C = concentration in g/100 ml.

Dyeing: The filaments were heated to boiling point over a period of 1 hour with 2% by weight of a red dye (Colour Index No. 23 635) in 1% acetic acid solution.

The parts and percentages quoted in the Examples are parts and percentages by weight, unless otherwise indicated.

EXAMPLE 1

N-Methoxymethyl-N'-2,2,6,6-tetramethyl piperidin-4-yl urea 31 g (0.2 mole) of 4-amino-2,2,6,6-tetramethyl piperidine were dissolved in 100 ml of toluene, followed by the dropwise addition while cooling with ice of 17.5 g (0.2 mole) of methoxymethyl isocyanate. The solvent was then evaporated in vacuo, leaving 48 g (99% of the theoretical yield) of a solid colourless product with a melting point of 96° C.

$C_{12}H_{25}N_3O_2$(243.4)
calculated: C 59.3% H 10.4% N 17.3%.
Observed: C 59.2% H 10.1% N 17.5%.

EXAMPLE 2

Hydroxymethyl-2,2,6,6,-tetramethyl piperidin-4-yl urea.HCl 19.9 g of 2,2,6,6-tetramethyl piperidin-4-yl urea.HCl (obtained from 2,2,6,6-TMP-HCl with KOCN; m.p. > 300° C.) were introduced into a mixture of 13.4 g of 37% formalin solution and 20 g of water, and the resulting mixture was stirred for 24 hours at room temperature. The crystals formed were then filtered off under suction and recrystallised from a liberal amount of methanol. 16.0 g of colourless, glossy needles melting at 263° to 265° C. (decomposition) were obtained. The product is readily soluble in water, moderately soluble in methanol and sparingly soluble to very sparingly soluble in all other organic solvents.

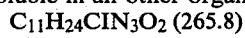
$C_{11}H_{24}ClN_3O_2$ (265.8)
Calculated: C 49.7% H 9.1% N 15.8% Cl 13.3%.
Observed: 49.3% 8.9% 15.8% 13.5%.

EXAMPLES 3 TO 12

The methoxymethyl ureas XIII summarised in Table 1 were obtained in the same way as described in Example 1 by reacting the corresponding 4-alkylamino- 2,2,6,6-tetramethyl piperidines with methoxymethyl isocyanate:

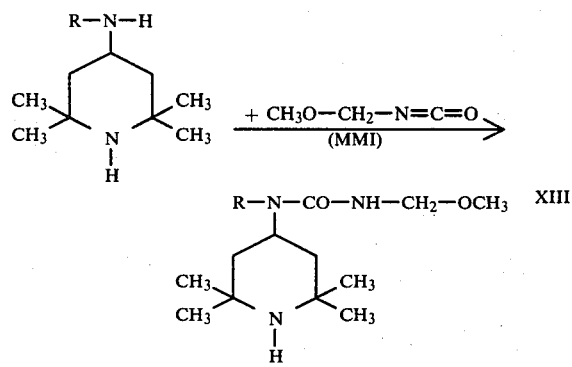

Procedure for producing the starting material of Example 5

(XIII, R = —CH$_2$—CH$_2$—CH$_2$—NH$_2$)

4-(γ-Aminopropyl)-amino-2,2,6,6-tetramethylpiperidine

A mixture of 131 parts of the nitrile R=—CH$_2$—CH$_2$—CN, 600 parts of methanol, 150 parts of liquid NH$_3$ and 25 parts of Ra-Co were hydrogenated at 80° C. to 100° C./80 to 100 bars H$_2$ until the uptake of hydrogen had ceased. After the catalyst had been filtered off, the mixture was fractionated in vacuo, giving 120 parts (89.6% of the theoretical yield) of 4-(γ-aminopropyl)-amino-2,2,6,6-tetramethyl piperidine in the form of a colourless liquid boiling at 95° C./0.1 Torr.

Table 1

| Example No. | XIII. R | Melting point (°C.) | Yield | Elemental analysis | | | | | | |
|---|---|---|---|---|---|---|---|---|---|---|
| 3 | —CH$_2$—CH$_2$—CO$_2$C$_2$H$_5$ | resin | 96% | calculated: observed: | C | 59.5 59.3 | H | 9.6 9.5 | N | 12.2 12.1 |
| 4 | —CH$_2$—CH$_2$—CN | 129° | 91% | calculated: observed: | C | 60.8 60.7 | H | 9.5 9.6 | N | 18.9 18.9 |
| 5 | —(CH$_2$)$_3$—NH—C(=O)—NH—CH$_2$OCH$_3$ (use twice the quantity of MMI) | 147° | 91% | calculated: observed: | C | 55.8 55.7 | H | 9.6 9.4 | N | 17.8 17.8 |
| 6 | -nC$_6$H$_{13}$— | resin | 98% | calculated: observed: | C | 66.0 65.9 | H | 11.4 11.6 | N | 12.8 12.0 |
| 7 | -nC$_3$H$_7$ | 136°-138° | 66% | calculated: observed: | C | 63.2 63.4 | H | 11.0 11.1 | N | 14.7 14.5 |
| 8 | -nC$_{12}$H$_{25}$ | oil | 99% | calculated: observed: | C | 70.0 68.3 | H | 12.0 11.5 | N | 10.2 9.8 |
| 9 | ⟨H⟩ | 118° | 91.5% | calculated observed: | C | 66.4 65.6 | H | 10.8 10.3 | N | 12.9 13.0 |
| 10 | —CH$_2$—CH$_2$OH | oil | 98% | calculated: observed: | C | 58.5 58.7 | H | 10.2 10.1 | N | 14.6 14.6 |
| 11 | —CH$_2$—CH(CH$_3$)$_2$ | 126° | 93.5% | calculated: observed: | C | 64.3 64.6 | H | 11.1 11.0 | N | 14.0 14.2 |
| 12 | —CH(CH$_3$)CH$_2$CH(CH$_3$)$_2$ | 71° | 99% | calculated: observed: | C | 66.0 66.1 | H | 11.4 11.2 | N | 12.8 12.8 |

Procedure for producing the starting material of Example 3

(XIII, R=CH$_2$—CH$_2$—COO—C$_2$H$_5$)

β-(2,2,6,6-Tetramethylpiperidin-4-yl)-aminopropionic acid ethyl ester 31.4 parts of amino-2,2,6,6-tetramethyl-piperidine and 100 parts of ethylacrylate were boiled under reflux for 5 hours and the mixture was subsequently fractionated in vacuo. β-(2,2,6,6-Tetramethylpiperidin-4-yl)-aminopropionic acid ethyl ester boiling at 112°-115° C./0.06 Torr was obtained in a yield of 43 parts (84% of the theoretical yield).

Procedure for producing the starting material of Example 4

(XIII, R = —CH$_2$—CH$_2$—CN)

β-(2,2,6,6-Tetramethylpiperidin-4-yl)-aminopropionitrile 156 parts of 4-amino-2,2,6,6-tetramethylpiperidine and 132.5 parts of acrylonitrile were stirred for 3.5 hours at 80° C. and the mixture was subsequently fractionated in vacuo, giving 190 parts (90.8% of the theoretical yield) of the nitrile in the form of a colourless liquid boiling at 107°-110° C./0.04 Torr.

C$_{12}$H$_{27}$N$_3$ (213.4).

EXAMPLE 13

(a) Procedure for producing the starting material: 2,2,6,6-Tetramethyl-4-hydroxypiperidine-4-carboxylic acid hydrazide 16.2 parts of 2,2,6,6-tetramethyl-4-hydroxypiperidine-4-carboxylic acid methyl ester (according to German Patent No. 91,122), 5 parts of hydrazine hydrate and 20 parts of methanol were boiled under reflux for 10 hours and the methanol was subsequently distilled off. The residue was recrystallised from cyclohexane. Yield: 15.3 parts of 2,2,6,6-tetramethyl-4-hydroxypiperidine-4-carboxylic acid hydrazide melting at 121° to 123° C.

C$_{10}$H$_{21}$N$_3$O$_3$ (231.3).

(b) Stabiliser according to the invention 4.62 parts (20 mMole) of the carboxylic acid hydrazide produced as described above were dissolved in 10 parts of dimethyl formamide and reacted with 0.174 parts (20 mMole) of methoxymethyl isocyanate in 7 parts of dimethyl formamide to form the methoxymethyl urea derivative. (an oily substance was left after removal of the solvent). Stabilisation was obtained by adding the solution of the derivatives thus produced to the elastomer solution.

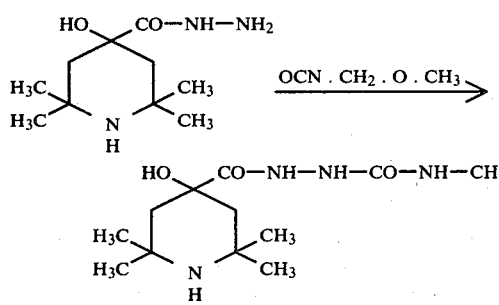

EXAMPLE 14

N-Methoxymethyl-O-2,2,6,6-tetramethylpiperidin-4-yl urethane 53.3 parts of 4-hydroxy-2,2,6,6-tetramethylpiperidine and 40 parts of methoxymethyl isocyanate were dissolved in 500 parts of methylene chloride with addition of 1 part of triethylene diamine and the resulting mixture was boiled under reflux for 150 hours. Excess methoxymethyl isocyanate and methylene chloride was then evaporated off, and the residue was recrystallised from petrol, giving colourless crystals melting at 110° to 112° C. Yield: 45 parts=56% of the theoretical yield. $C_{12}H_{24}N_2O_3$ (244.3).

EXAMPLE 15

(a) Procedure for producing the starting material

β-(2,2,6,6-Tetramethylpiperidin-4-yl)-aminopropionic acid hydrazide.

51.2 parts of the ester according to (XIII, R=CH₂—CH₂—CO₂—C₂H₅) and 20 parts of hydrazine hydrate were boiled under reflux for 16 hours in 100 parts of alcohol. Removal of the alcohol by evaporation left 48 parts (100% of the theoretical yield) of the hydrazide in the form of a colourless, tacky crystal mass.

$C_{12}H_{26}N_4O$ (242.4)

Calculated: C 59.5% H 10.8% N 23.1%
Observed: C 59.6% H 10.6% N 23.2%

(b) Compound according to the invention

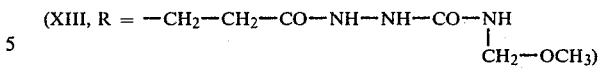

36.3 parts of β-(2,2,6,6-tetramethylpiperidin-4-yl)-aminopropionic acid hydrazide were dissolved in 100 parts of toluene, followed by the dropwise addition of 28.2 parts of 93% methoxymethyl isocyanate. After stirring for 1 hour at 25° C., the deposit was filtered off under suction. The filter residue was stirred with 300 parts of petroleum ether and refiltered under suction. 48 parts of colourless crystals melting at 62° to 65° C. were left after drying.

$C_{18}H_{36}N_6O_5$ (416.5).

EXAMPLE 16

1.25 ml of a 30% sulphur dioxide solution in dioxane were added to 600 parts of an adipic acid copolyester (molecular weight 1915) with 65 mole % of 1,6-hexane diol and 35 mole % of 2,2-dimethyl propane diol, followed by dehydration for 1 hour in vacuo at 130° C.

Following the addition of 12.15 parts of N-methyl-bis-(β-hydroxypropyl)-amine to the polyester, a solution of 168.15 parts of diphenyl methane-4,4′-diisocyanate in 195 parts of dimethyl formamide was added at 40° C., followed by heating for 60 minutes at 50° to 53° C. to form the prepolymer (2.715% of NCO in the solids).

10 parts of solid carbon dioxide were added to a solution of 3.35 parts of 99% ethylene diamine in 449 parts of dimethyl formamide to form the carbamate, after which 210 parts of the above NCO-prepolymer solution were introduced and 0.10 part of hexane-1,6-diisocyanate was added. The elastomer solution (790 Poises) was pigmented with 4% of TiO₂ (Rutil FD-2, a product of Bayer AG).

The following stabilisers were added to prportions of the solutions:

(a) comparison, no stabiliser added
(b) 2% Tinuvin ® 770 (a product of Ciba-Geigy)-Comparison Test

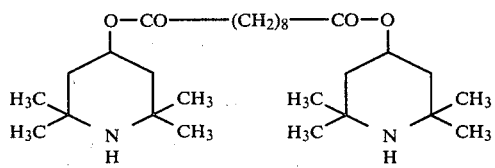

(c) 2% of a stabiliser combination corresponding to the formula

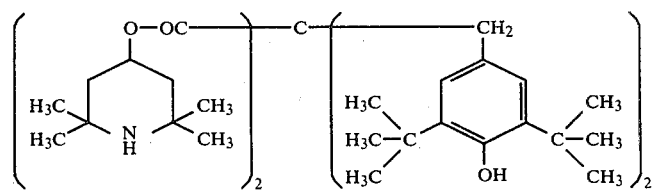

Comparison test m.p. 215°–217° C.
(a stabiliser combination which is sparingly soluble in water and substantially insoluble in petroleum ether).

(d) 2% of attachable stabiliser according to Example 11 (+0.4% of citric acid)

(e) 2% of double reactive-stabiliser according to Example 5 (+0.4% of citric acid)

(f) 2% of stabiliser according to Example 1-catalyst 0.4% of citric acid +1% of Irganox 1010 (a product of Ciba-Geigy) +1% of Tinuvin 327 (a product of Ciba-Geigy; benztriazole UV-absorber)

(g) 0.33% of stabiliser according to Example 1 +1% of Irganox 1010 +1% of Tinuvin 327

(h) 2% of Tinuvin 770 (comparison test) +1% of Irganox 1010 +1% of Tinuvin 327.

The solutions were cast into films (drying at 70°/100°/130° C.), optionally sliced into filaments ("sliced filaments") or dry-spun (nozzle 16/0.2 mm; denier approx. 130 dtex.) and the filaments were subjected on bobbins to thermal aftertreatment agt 130° C. (or overheating godets—surface temperature 180° C.).

1. Dyeability test

The filaments (partly in the form of sliced filaments, partly in the form of dry-spun filaments) were dyed for 1 hour with the red dye (C.I. 23 635) and the dyed filaments were tested while wet for their abrasion resistance (see Table 2). Whereas the elastomer filaments modified with the attachable stabilisers in accordance with the present invention showed a normal affinity for dyes and gave abrasion-resistant dye finishes, the comparison tests with the stabilisers of the tetramethyl piperidine series according to the prior art led to considerable faults in dyeability and also to reduce abrasion resistance, obviously due to "dye salt" formation from basic stabiliser and acid dyes (tests b, c, h).

state; $\beta$ after extraction for 1 hour with carbon tetrachloride; $\gamma$ after boiling for 1 hour with 1% acetic acid solution. For discoloration, See Table 3

It was found that the originally good stabilising effect of the stabilisers according to (b) and (c) was almost completely lost by solvent extraction and boiling with weak acetic acid solution. By contrast, the stabilising effect of the stabilisers according to the invention (d), (e) remained almost fully intact.

Filaments dry spun from solutions with the following composition:
 (a) (without stabiliser)
 (d) stabiliser (1) according to the invention (g) (stabiliser 1 according to the invention) + phenolic stabiliser/UV-absorber
(k) (1% of phenolic stabiliser (IRGANOX 1010) (+1% of UV-absorber (TINUVIN 327) -as comparison test to g)- were exposed to light in a Fadeometer. The filaments were found to have the following residual strengths after exposure for 66 hours.

(a) <0.08 g/dtex—without stabiliser—
(d) 0.28 g/dtex (according to the invention)
(g) 0.51 g/dtex (according to the invention, synergistic effect)
(k) ~0.10 g/dtex—comparison —

Whereas filaments without the stabiliser according to the invention were heavily discoloured and totally degraded, the stabiliser according to the invention had a distinct stabilising effect, as reflected in a very clear increase in effect in the simultaneous presence of pheno-

Table 2

Dyeing with 2% Supranolechtrot-GG (acid dye) in weak acetic acid solution

| Filament composition | Type of filaments | Dye finish on the sliced filaments | After-absorption on wool | Abrasion resistance of the dyed elastomer filaments | Remarks |
|---|---|---|---|---|---|
| (a) | V | SF, DSF. | deep-red dye finish | light red | abrasion-resistant | (unstabilised types) |
| (b) | V | SF, DSF. | as (a), somewhat lighter than (a) | red | heavy abrasion | stabiliser migrates and probably forms deposits with dye |
| (c) | V | SF | light red, patchy | light red | very heavy abrasion | |
| (d) | | SF, DSF. | deep red | light red | abrasion-resistant | extraction-resistant stabilisation |
| (e) | | SF | deep red | light red | abrasion-resistant | |
| (f) | | SF, DSF. | deep red | light red | abrasion-resistant | |
| (g) | | SF | deep red | light red | abrasion-resistant | stabilized filaments |
| (h) | V | SF, DSF. | deep red | red | heavy abrasion | see (b)/(c) |

(SF = sliced filaments)
(V = comparison tests)
(DSF = dry spun filaments)

2. Testing for UV-stabiliser effect and resistance to extraction

Films with the compositions (a), (b), (c), (d), (e) were exposed to light in a Fadeometer: $\alpha$ in their original lic stabilisers and UV-stabilisers, even when the stabiliser according to the invention was added in a very small quantity.

Table 3

| Composition of film | | UV-exposure of films (Fadeometer) Discoloration after Fadeometer testing for | | | | | | | | Remarks |
|---|---|---|---|---|---|---|---|---|---|---|
| | | 22 hours | | | 44 hours | | | 88 hours | | |
| | | original (α) | CCl4 (β) | acetic acid (γ) | original (α) | CCl4 (β) | acetic acid (γ) | original (α) | CCl4 (β) | acetic acid (γ) | |
| (a) | (V) | yellowish yellow | yellowish yellow | yellowish yellow | yellow | yellow | yellow | yellow-brown | yellow-brown | yellow-brown | unstabilised |
| (b) | (V) | colourless | yellowish yellow | yellowish yellow | almost colourless | yellow | yellow | almost colourless | yellow-brown | yellow-brown | extractable stabilisers |
| (c) | (V) | colourless | yellowish yellow | yellowish yellow | almost colourless | yellow | yellow | almost colourless | yellow-brown | yellow-brown | |
| (d) | (xxx) | colourless | colourless | colourless | colourless | (almost)(x) colourless | colourless | colourless | (almost)(x) colourless | colourless | extraction-resistant stabilisers according to the invention |
| (e) | | colourless | colourless | colourless | colourless | colourless(xx) | colourless | colourless | colourless | colourless | |

(x) the film dried at 100° C. discolours slightly more easily (reaction sill not altogether complete) the film dried at 130° C. is substantially colourless (the stabiliser is fixed)
(xx) films no longer soluble in DMF
(xxx) the same results are obtained when only 0.5% of stabiliser according to Example 1 is added.

Proportions of the solutions according to Example 16 had added to them
(i) 1% by weight of the phenolic stabiliser

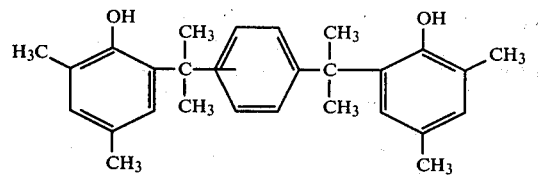

(m/p-isomeric mixture) +1% of Tinuvin 327 (a produce of Ciba-Geigy)

(k) 1% of the phenolic stabiliser according to i) + 1% of the stabiliser 1) according to the invention, after which the solutions were dry-spun through 16/0.2-nozzles, the elastomer filaments were run off from the spinning duct at 100 m/minute and, after preparation, were wound into package form at around 130 m/minute. The packages were heated for 1 hour to 130° C. and subsequently measured.

The following tensile strengths (in g/dtex) of the filaments (denier approximately 180 dtex, individual filament denier approximately 11 dtex) were obtained after Fadeometer testing for 0,22,44,66 and 88 hours.

| Before exposure (g/dtex) | after 22 hours | after 44 hours | after 66 hours |
|---|---|---|---|
| (i) 0.56 | 0.52 | 0.48 | 0.08 |
| (k) 0.56 | 0.62 | 0.63 | 0.47 |

The results showed the advantageous co-stabilising effect obtained with the stabiliser according to the invention in relation to conventional stabiliser mixtures.

EXAMPLE 17

400 parts of the hexane diol-neopentyl glycol-adipic acid polyester (MW 1915) (see Example 16) were mixed with 7.92 parts of N-methyl-bis(β-hydroxypropyl)-amine, the resulting mixture was heated for 50 minutes to 50° C. with a solution of 112 parts of diphenyl methane-4,4'-diisocyanate and is subsequently cooled. The NCO-prepolymer solution formed had an NCO-content of 2.865 % (based on solids).

11.68 parts of $H_2N-NH-CO-NH-CH_2-CH_2-CO'NH-NH_2$ were dissolved in 23 parts of water and the resulting solution was mixed with 580 parts of dimethyl formamide 268.75 parts of the above NCO-prepolymer were introduced into the mixture over a period of 3 minutes, resulting in the formation of a clear, highly viscous elastomer solution (~600 Poises) which was pigmented with 4% of $TiO_2$ "Rutil KB".

To proportions of the solution were added
(a) no stabiliser,
(b) 2.0% of stabiliser according to Example 1), based on solids,
(c) 0.5% of stabiliser according to Example 1), based on solids,
(d) 0.5% of Tinuvin 770, and films were prepared from the solution (drying temperature 100° C. or 130° C.). The films were sliced into filaments (approximately 350 dtex) and Fadeometer-tested α untreated,
β after extraction for 1 hour with boiling carbon tetrachloride, and
γ after boiling for 1 hour with 1% acetic acid solution.
The results are set out in Table 4.

The results confirmed the good stabilising effect of the stabilisers according to the invention which were not affected to any significant extent even by extraction treatments (the slight differences were partly attributable to some slight damage caused by the extraction treatments). By contrast, the conventional stabilised Tinuvin 770 was almost quantitatively removed by the extraction treatments.

Dyeing tests with 2% of the red acid dye (C.I. 23 635) showed good dyeability without any abrasion resistance problems in the case of the stabilisers according to the invention, whereas in cases where non-incorporable stabilisers according to the prior art were added the (somewhat inferior) dye finish is virtually non-resistant to abrasion (see also Examples 16, 18).

EXAMPLE 28

Bis-methoxymethyl urea stabiliser corresponding to the formula

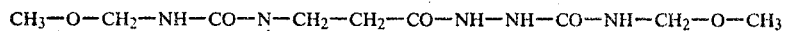
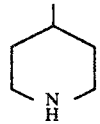

36.3 parts of β-(2,2,6,6-tetramethylpiperidin-4-yl)-aminopropionic acid hydrazide were dissolved in 100 parts of toluene, followed by the dropwise addition of 28.2 parts of 93% methoxymethyl isocyanate. After stirring for 1 hour at 25° C., the deposit was filtered off under suction. The filter residue was stirred with 300 parts of petroleum ether and refiltered under suction. 48 parts of colourless crystals melting at 62° to 65° C. were left after drying. $C_{18}H_{36}N_6O_5$ (416.5).

EXAMPLE 29

(a) 15.6 parts of 4-amino-2,2,4,4-tetramethylpiperidine dissolved in 293 parts of ethanol were added dropwise over a period of 100 minutes to a solution cooled to 5°–10° C. of 21.4 parts of diphenyl carbonate in 427 parts of ethanol which was then left standing overnight and subsequently heated for 5 hours at 50° to 70° C.

(b) 802 parts of solution (a) containing the phenyl urethane α,

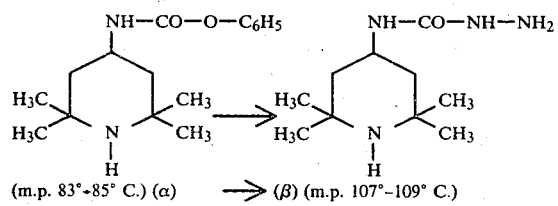

were mixed with a solution of 5.62 parts of hydrazine hydrate in 50 parts of ethanol, the resulting mixture was left standing overnight and was then subsequently heated for 3 hours at 50° to 60° C. Removal of the solvent by distillation left an oily residue which quickly crystallised out. After dissolution in benzene and precipitation with petroleum ether, the substance crystallised. Softening range: 93° to 98° C., m.p. after recrystallisation from boiling water: 107° to 109° C.

(c) Stabiliser according to the invention containing terminal methylol ether groups:

0.87 parts of methoxymethyl isocyanate in 12 parts of dimethyl formamide was added dropwise to 2.14 parts of the semicarbazide (β) dissolved in 15 parts of dimethyl formamide.

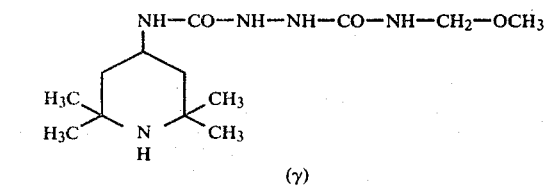

(d) Stabilisation:

2% by weight of stabiliser γ (as solution c), based on solids) were mixed into an elastomer solution produced in the same way as described in Example 18, the solution was cast into films (drying 100° C./130° C.) and the films thus produced were Fadeometer-tested. The stabilisation obtained was substantially identical with the stabilisation according to Example 18c); it was similarly resistant to extraction.

EXAMPLE 30

(a) 17.0 parts of 4-amino-1,2,2,6,6-pentamethylpiperidine, dissolved in 300 parts of ethanol, were added dropwise over a period of 100 minutes at 5° to 10° C. to a solution of 21.4 parts of diphenyl carbonate in 527 parts of ethanol, followed by heating for 5 hours at 50° to 70° C. (A sample crystallises from petroleum ether with a melting point of 122° to 125° C.).

(b) 815 parts of solution (a), containing the phenyl urethane δ), were mixed with a solution of 5.65 parts of hydrazine hydrate in 50 parts of ethanol, the resulting mixture was left standing overnight and was then heated for 3 hours at 60° C.

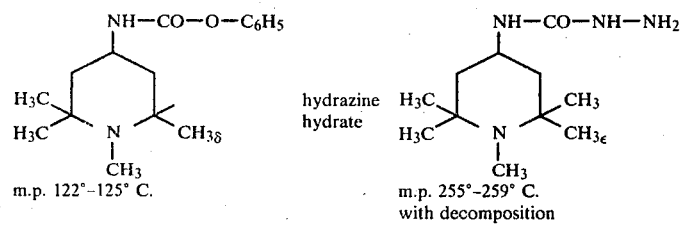

(c) 2.28 parts of the 1,2,2,6,6-pentamethylpiperidinone-4-semicarbazide (ε) were dissolved in 15 parts of dimethyl formamide, followed by the addition of 0.87 parts of methoxymethyl isocyanate in 13.35 parts of dimethyl formamide. The solution of the methylol ether derivative formed (τ)

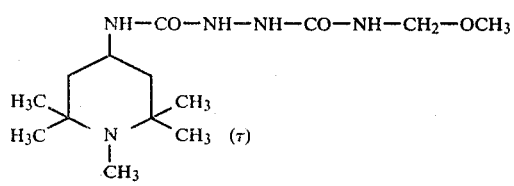

was directly used for stabilisation.

(d) Stabilisation:

2% by weight of stabiliser (as solution c, based on solids) were mixed into an elastomer solution produced in the same way as described in Example 18, and the solution was dried to form films (film drying 30 minutes at 100° C./130° C. The stabilisation obtained was resistant to extraction and was substantially equal in its effectiveness to the stabilisation obtained with the N-H-piperidine derivative (γ) of Example 29.

EXAMPLE 31

(a) NCO-prepolymer formation 1000 parts of a polytetramethylene ether diol (molecular weight 2000), 18.9 parts of N-methyl-bis-(β-hydroxypropyl)amine, 246.1 parts of diphenyl methane-4,4'-diisocyanate and 317 parts of dimethyl formamide were heated at 40° to 45° C. until the NCO-content amounted to 2.265% (based on solids).

(b) Chain extension with β-semicarbazidopropionic acid hydrazide (Comparison Example)

7.47 parts of β-semicarbazidopropionic acid hydrazide, dissolved in 15 parts of water and 541 parts of dimethyl formamide, were stirred with 215 parts of the NCO-preadduct solution according to (a) and pigmented with 4% of TiO₂ (based on solids). A viscous solution (600 Poises/ηi=1.01) was obtained.

(c) Addition according to the invention of the attachable stabiliser according to Example 23(b)

1.0% by weight (based on solids) of the stabiliser according to Example 23b was added to solution (b). Films were cast from solutions (b) and (c) (drying for 60 minutes at 100° C.).

The films were Fadeometer tested for 22, 44, 88, 110, 132 and 154 hours both in their original state and after extraction for 1 hour with perchlorethylene at 50° C. Whereas the stabiliser-free film (b) was yellow and had retained less than 15% of its original strength after only 22 hours, the stabilised film (c) remained colourless and retained its strength for up to 154 hours, being fully elastic and free from surface cracks after stretching. The stabilising effect was not eliminated by treatment with perchlorethylene. The stabilising effect of the derivatives methylated on the piperidine nitrogen (R=CH₃) was substantially equal to the stabilising effect of the derivatives unsubstituted on the piperidine ring (R=H).

Additions of 1% of the stabilisers according to Examples 24(b), 25(b), 26(b) and 27(b) produced as good and as extraction-resistant a stabilising effect as did stabiliser 23(b) in film (c).

When 1% by weight of stabiliser according to Example 28 was added and the film heated at 130° C., the films obtained were again effectively stabilised, but were insoluble in dimethyl formamide and were particularly suitable for coatings, for example.

What we claim is:

1. A compound of the formula

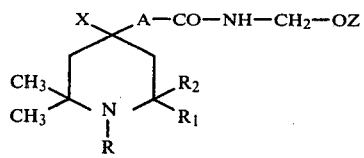

wherein
A is

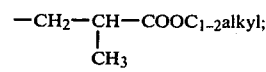

wherein $R_3$ is $C_1$-$C_{20}$-alkyl, hydrogen, $C_5$-$C_{12}$-cycloalkyl or $C_7$-$C_{12}$-aralkyl and E is a direct bond;

Z is hydrogen or $C_1$-$C_{14}$-alkyl;

R is hydrogen, $C_1$-$C_{20}$-alkyl, $C_3$-$C_5$-alkenyl; $C_7$-$C_{12}$-aralkyl; CH—CHR₆—OH, wherein R₆ is hydrogen, methyl, or phenyl; —CH₂CH₂CN; —CH₂—CH₂—COOC₁₋₂alkyl; or $$-CH_2-\underset{\underset{CH_3}{|}}{CH}-COOC_{1-2}alkyl;$$

$R_1$ and $R_2$ independently of one another are $C_1$-$C_6$-alkyl, or $R_1$ and $R_2$ together with the ring carbon atom to which they are attached form $C_1$-$C_7$-cycloalkyl; and X is hydrogen.

2. The compound of claim 1, wherein

R is hydrogen or methyl;

$R_1$ and $R_2$ are each methyl; and

Z is methyl.

3. The compound of claim 1 wherein $R_3$ is hydrogen, $C_1$-$C_8$-alkyl or cyclohexyl.

4. The compound of claim 1, wherein Z is H or methyl.

5. A process for the production of the compound of claim 1, comprising reacting a compound of the formula

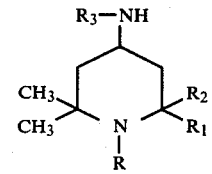

with (a) cyanic acid and then (b) formaldehyde to react each NH group not attached to the ring with cyanic acid to form first a —N—CO—NH₂— group and subsequently an —N—CO—NH—CH₂OH group or (c) additionally etherifying the —N—CO—NH—CH₂OH group with an alcohol of the formula ZOH in acid medium.

* * * * *

Table 6-continued

| Stabiliser according to Example No. (Comparison) | Quantity added | | Fadeometer testing of films with and without extraction Discoloration after Fadeometer testing (in hours) | | | | |
|---|---|---|---|---|---|---|---|
| | | | 44 | 66 | 88 | 110 | 154 |
| | none | α | yellow | yellow | yellow-brown | yellow-brown | brown |
| | | γ | " | colourless | colourless | almost colourless | colourless almost colourless |
| 9 | 2% | α | colourless | colourless | colourless | colourless | almost colourless |
| | | β/a | " | almost colourless | almost colourless | almost colourless | yellowish |
| | | γ | " | " | " | " | almost colourless |
| 10 | 2% | α | colourless | colourless | colourless | colourless | almost colourless |
| | | β/a | " | " | " | almost colourless | almost colourless |
| | | γ | " | " | " | " | " |
| 11 | 2% | α | colourless | almost colourless | — | almost colourless | yellow |
| | | β/a | " | " | — | " | " |
| | | γ | " | " | — | yellowish | " |
| 12 | 2% | α | colourless | colourless | — | — | — |
| | | β/a | " | " | — | — | — |
| | | γ | " | " | — | — | — |
| 13 | 2% | α | colourless | colourless | colourless | colourless | almost colourless |
| | | β/a | " | " | " | almost colourless | " |
| | | γ | " | " | " | colourless | " |
| 14 | 2% | α | almost colourless | yellowish | yellow | yellow-brown | — |
| 15 | 2% | α | colourless | colourless | almost colourless | almost colourless | — |

EXAMPLE 20

A copolyamide (polycondensed from 50 parts of caprolactam, 35 parts of 66-salt and 20 parts of 6,10-salt) was dissolved in a mixture of 85 parts by weight of methanol, 6 parts by weight of isopropanol, 4.5 parts by weight of isobutanol and 4.5 parts by weight of water to form an approximately 12% solution.

Proportions of the solutions were cast into thin films
(a) without stabiliser added;
(b) with 0.4% of Tinuvin 770 added (Comparison);
(c) with 0.4% of stabiliser according to Example 1 added, the films thus cast were dried for 1 hour at 130° C. in a drying cabinet and Fadeometer-tested for 300 hours. The stabiliserfree copolyamide (a) was embrittled and broke when the film was flexed; films (b) and (c) had remained flexible.

However, when films (b) and (c) were treated for 24 hours with a 2.5% acetic acid solution and then for 5×30 minutes with perchlorethylene at 50° C. and subsequently exposed to light, film (b) also became fragile, whilst film (c) remained flexible.

EXAMPLE 21

600 parts of a 1,6-hexane diol polycarbonate (molecular weight 1925) were heated for about 220 minutes to 97° C. with 138.5 parts of 1-isocyanato-3-isocyanatomethyl-3,5,5-trimethyl cyclohexane and 185.5 parts of the aromatic hydrocarbon mixture "Solvesso-100" (a product of SHELL), resulting in the formation of an NCO-prepolymer solution with an NCO-content of 3.58% (based on solids).

4.2 parts of 1,4-diaminocyclohexane (17.3% of cis-/82.7% of trans-isomer) were introduced into 233 parts of Solvesso/ ethylene glycol (1:1), followed by the introduction with stirring of 107.5 parts of the prepolymer solution. The homogeneous solution (266 Poises/20° C.) was cast into films with and without stabiliser added and the films thus cast were briefly dried at around 150° C. in a drying tunnel.

Although the aliphatic polyurethane (used for coating compositions and finishes for artificial leather) remained colourless on exposure to light, its tensile strength decreased. The stabiliser added in accordance with the invention retarded the degradation process to a considerable extent. The effect of the stabiliser was not reduced by treatment for 2×30 minutes with perchlorethylene, the films having become insoluble.

Table 6

| | Original TS g/dtex | after 154 Fadeometer hours |
|---|---|---|
| without stabiliser | 0.69 | 0.29 |
| with 0.4% of stabiliser according to Example 5 +0.1% of monochloroacetic acid | 0.69 | 0.64 |

EXAMPLE 22

100 parts of GL-N-Resin granulate, an almost completely hydrolysed ethylene-vinylacetate copolymer containing approximately 85% by weight of vinylacetate before hydrolysis (manufacturers: Nippon Synthetic Chemical Industry Co., Ltd. Japan) were softened for 24 hours in 400 parts of dimethyl acetamide and then dissolved for 6 hours at 80° C. and for 2 hours at 100° C.

0.5% of stabiliser 1 according to the invention (based on polymer solids) was added to proportions of the 20% solution, after which the solution was dried to form approximately 0.15 mm thick films (45 minutes at 70° C.+90 minutes at 100° C.). Some of the films were boiled for 1 hour with carbon tetrachloride. A film of GL-N-Resin without any stabiliser added was Fadeometer tested for 550 hours for comparison with the stabilised films. Whereas the unstabilised film broke as a result of embrittlement, the stabilised films were still colourless and completely flexible. The stabilisation according to the invention was resistant to extraction.

EXAMPLE 23

(a) 1,2,2,6,6-Pentamethyl-4-aminopiperidine (starting material)

750 parts of 4-benzoylamine-1,2,2,6,6-pentamethyl piperidine were dissolved in 1000 parts of concentrated hydrochloric acid and the resulting solution boiled under reflux for 10 hours. After cooling, sodium hydroxide was added until an alkaline reaction was obtained and the mixture was repeatedly extracted with methylene chloride. The residue obtained after removal of the methylene chloride by evaporation was distilled in vacuo, 300 parts of 1,2,2,6,6-pentamethyl-4-aminopiperidine boiling at 98° C./15 Torr distilling over.

(b) N-Methoxymethyl-N'-(1,2,2,6,6-pentamethylpiperidin-4-yl)-urea (Compound according to the invention)

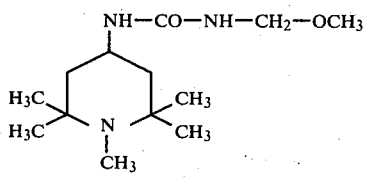

34 parts of 1,2,2,6,6-pentamethyl-4-aminopiperidine were dissolved in 100 parts of toluene, followed by the dropwise addition of 25° C. of 18.8 parts of 93% methoxymethyl isocyanate. After stirring for 1 hour at 25° C., the toluene was evaporated in vacuo and the residue was crystallised from cleaning spirit, giving 42.5 g of colourless crystals melting at 105° C.

$C_{13}H_{27}N_3O_2$ (257.4)
calculated: C 60.7% H 10.6% N 16.3%.
observed: 60.7% 10.1% 16.3%.

42.1 parts of N-methoxymethyl-N'-1,2,2,6,6-pentamethylpiperidin-4-yl urea were obtained in the same way using 26.2 parts of methoxymethyl acetonitrile carbonate instead of 18.8 parts of 93% methoxymethyl isocyanate.

EXAMPLE 24

(a) 4-Amino-1-allyl-2,2,6,6-tetramethylpiperidine (starting material)

164 parts of 4-amino-1-allyl-2,2,6,6-tetramethylpiperidine (b.p. 112° C./15 Torr) were obtained from 300 parts of 4-benzoylamino-1-allyl-2,2,6,6-tetramethylpiperidine by the same hydrolysis reaction as described in Example 23a.

(b) N-methoxymethyl-N'-(1-allyl-2,2,6,6-tetramethylpiperidin-4-yl)-urea (Compound according to the invention)

50 parts of N-methoxymethyl-N'-1-allyl-2,2,6,6-tetramethylpiperidin-4-yl urea were obtained in the same way as described in Example 23b) using 39 parts of 4-amino-1-allyl-2,2,6,6-tetramethylpiperidine.

EXAMPLE 25

(a) 4-Amino-1-ethyl-2,2,6,6-tetramethylpiperidine (starting material)

130 parts of 4-amino-1-ethyl-2,2,6,6-tetramethylpiperidine boiling at 105°–107° C./15 Torr were obtained from 288 parts of 4-benzoylamino-1-ethyl-2,2,6,6-tetramethylpiperidine by the same hydrolysis reaction as described in Example 22(a).

(b) N-Methoxymethyl-N'-(1-ethyl-2,2,6,6-tetramethyl-piperidine-4-yl)-urea (stabiliser according to the invention)

46 parts of N-methoxymethyl-N'-1-ethyl-2,2,6,6-tetramethylpiperidin-4-yl urea were obtained by reacting 36.6 parts of 4-amino-1-ethyl-2,2,6,6-tetramethylpiperidine with methoxymethyl isocyanate in the same way as described in Example 22b).

EXAMPLE 26

(a) 4-Amino-1-benzyl-2,2,6,6-tetramethylpiperidine (starting material)

218 parts of 4-amino-1-benzyl-2,2,6,6-tetramethylpiperidine boiling at 110° C./0.1 Torr were obtained from 350.5 parts of 4-benzoylamino-1-benzyl-2,2,6,6-tetramethylpiperidine by the same hydrolysis reaction as described in Example 23(a).

(b) N-Methoxymethyl-N'-(1-benzyl-2,2,6,6-tetramethyl-piperidin-4-yl)-urea (Compound according to the invention)

51 parts of N-methoxymethyl-N'-1-benzyl-2,2,6,6-tetramethylpiperidin-4-yl urea were obtained by reacting 49.1 parts of 4-amino-1-benzyl-2,2,6,6-tetramethylpiperidine with methoxymethyl isocyanate in the same way as described in Example 23(b).

EXAMPLE 27

(a) 4-(β-Cyanoethyl)-amino-1,2,2,6,6-pentamethylpiperidine (starting material)

132.5 parts of acrylontrile were added dropwise to 170 parts of 1,2,2,6,6-pentamethyl-4-aminopiperidine. After stirring for 3 hours at 70° C., the mixture was fractionated in vacuo, giving 180 parts of 4-(β-cyanoethyl)-amino-1,2,2,6,6-pentamethylpiperidine boiling at 115° to 117° C./0.08 Torr.

(b) N-Methoxymethyl-N'-(β-cyanoethyl)-N'-1,2,2,6,6-pentamethylpiperidin-4-yl)-urea (Compound according to the invention)

A partially crystalline mass was obtained in a substantially quantitative yield by reacting methoxymethyl isocyanate with 44.6 parts of 4-(β-cyanoethyl)-amino-1,2,2,6,6-pentamethylpiperidin in the same way as described in Example 23b) and distilling off the solvent.

EXAMPLE 28

Bis-methoxymethyl urea stabiliser corresponding to the formula

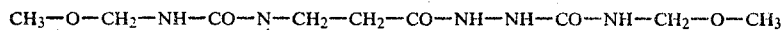
CH₃—O—CH₂—NH—CO—N—CH₂—CH₂—CO—NH—NH—CO—NH—CH₂—O—CH₃

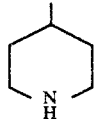

36.3 parts of β-(2,2,6,6-tetramethylpiperidin-4-yl)-aminopropionic acid hydrazide were dissolved in 100 parts of toluene, followed by the dropwise addition of 28.2 parts of 93% methoxymethyl isocyanate. After stirring for 1 hour at 25° C., the deposit was filtered off under suction. The filter residue was stirred with 300 parts of petroleum ether and refiltered under suction. 48 parts of colourless crystals melting at 62° to 65° C. were left after drying. $C_{18}H_{36}N_6O_5$ (416.5).

EXAMPLE 29

(a) 15.6 parts of 4-amino-2,2,4,4-tetramethylpiperidine dissolved in 293 parts of ethanol were added dropwise over a period of 100 minutes to a solution cooled to 5°–10° C. of 21.4 parts of diphenyl carbonate in 427 parts of ethanol which was then left standing overnight and subsequently heated for 5 hours at 50° to 70° C.

(b) 802 parts of solution (a) containing the phenyl urethane α,

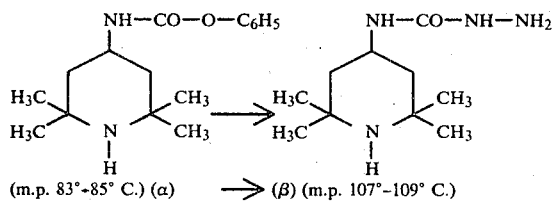
(m.p. 83°-85° C.) (α) ⟶ (β) (m.p. 107°-109° C.)

were mixed with a solution of 5.62 parts of hydrazine hydrate in 50 parts of ethanol, the resulting mixture was left standing overnight and was then subsequently heated for 3 hours at 50° to 60° C. Removal of the solvent by distillation left an oily residue which quickly crystallised out. After dissolution in benzene and precipitation with petroleum ether, the substance crystallised. Softening range: 93° to 98° C., m.p. after recrystallisation from boiling water: 107° to 109° C.

(c) Stabiliser according to the invention containing terminal methylol ether groups:

0.87 parts of methoxymethyl isocyanate in 12 parts of dimethyl formamide was added dropwise to 2.14 parts of the semicarbazide (β) dissolved in 15 parts of dimethyl formamide.

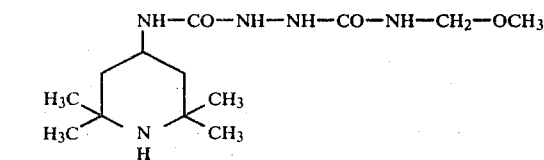
(γ)

(d) Stabilisation:

2% by weight of stabiliser γ (as solution c), based on solids) were mixed into an elastomer solution produced in the same way as described in Example 18), the solution was cast into films (drying 100° C./130° C.) and the films thus produced were Fadeometer-tested. The stabilisation obtained was substantially identical with the stabilisation according to Example 18c); it was similarly resistant to extraction.

EXAMPLE 30

(a) 17.0 parts of 4-amino-1,2,2,6,6-pentamethylpiperidine, dissolved in 300 parts of ethanol, were added dropwise over a period of 100 minutes at 5° to 10° C. to a solution of 21.4 parts of diphenyl carbonate in 527 parts of ethanol, followed by heating for 5 hours at 50° to 70° C. (A sample crystallises from petroleum ether with a melting point of 122° to 125° C.).

(b) 815 parts of solution (a), containing the phenyl urethane δ), were mixed with a solution of 5.65 parts of hydrazine hydrate in 50 parts of ethanol, the resulting mixture was left standing overnight and was then heated for 3 hours at 60° C.

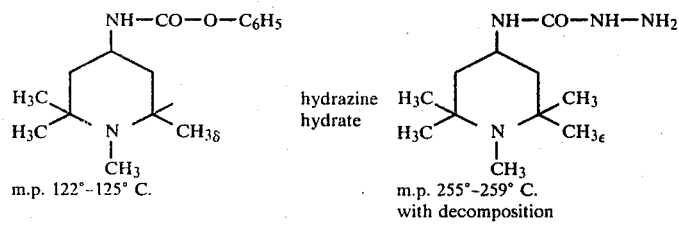
m.p. 122°-125° C.    m.p. 255°-259° C. with decomposition (c) 2.28 parts of the 1,2,2,6,6-pentamethylpiperidinone-4-semicarbazide (ε) were dissolved in 15 parts of dimethyl formamide, followed by the addition of 0.87 parts of methoxymethyl isocyanate in 13.35 parts of dimethyl formamide. The solution of the methylol ether derivative formed (τ)

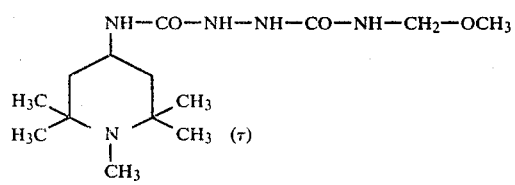
(τ)

was directly used for stabilisation.

(d) Stabilisation:

2% by weight of stabiliser (as solution c, based on solids) were mixed into an elastomer solution produced in the same way as described in Example 18, and the solution was dried to form films (film drying 30 minutes at 100° C./130° C. The stabilisation obtained was resistant to extraction and was substantially equal in its effectiveness to the stabilisation obtained with the N-H-piperidine derivative (γ) of Example 29.

EXAMPLE 31

(a) NCO-prepolymer formation 1000 parts of a polytetramethylene ether diol (molecular weight 2000), 18.9 parts of N-methyl-bis-(β-hydroxypropyl)amine, 246.1 parts of diphenyl methane-4,4'-diisocyanate and 317 parts of dimethyl formamide were heated at 40° to 45° C. until the NCO-content amounted to 2.265% (based on solids).

(b) Chain extension with β-semicarbazidopropionic acid hydrazide (Comparison Example)

7.47 parts of β-semicarbazidopropionic acid hydrazide, dissolved in 15 parts of water and 541 parts of dimethyl formamide, were stirred with 215 parts of the NCO-preadduct solution according to (a) and pigmented with 4% of $TiO_2$ (based on solids). A viscous solution (600 Poises/ηi=1.01) was obtained.

(c) Addition according to the invention of the attachable stabiliser according to Example 23(b)

1.0% by weight (based on solids) of the stabiliser according to Example 23b was added to solution (b). Films were cast from solutions (b) and (c) (drying for 60 minutes at 100° C.).

The films were Fadeometer tested for 22, 44, 88, 110, 132 and 154 hours both in their original state and after extraction for 1 hour with perchlorethylene at 50° C. Whereas the stabiliser-free film (b) was yellow and had retained less than 15% of its original strength after only 22 hours, the stabilised film (c) remained colourless and retained its strength for up to 154 hours, being fully elastic and free from surface cracks after stretching. The stabilising effect was not eliminated by treatment with perchlorethylene. The stabilising effect of the derivatives methylated on the piperidine nitrogen (R=$CH_3$) was substantially equal to the stabilising effect of the derivatives unsubstituted on the piperidine ring (R=H).

Additions of 1% of the stabilisers according to Examples 24(b), 25(b), 26(b) and 27(b) produced as good and as extraction-resistant a stabilising effect as did stabiliser 23(b) in film (c).

When 1% by weight of stabiliser according to Example 28 was added and the film heated at 130° C., the films obtained were again effectively stabilised, but were insoluble in dimethyl formamide and were particularly suitable for coatings, for example.

What we claim is:

1. A compound of the formula

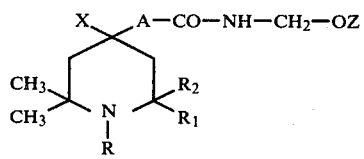

wherein
A is

wherein $R_3$ is $C_1$-$C_{20}$-alkyl, hydrogen, $C_5$-$C_{12}$-cycloalkyl or $C_7$-$C_{12}$-aralkyl and E is a direct bond;

Z is hydrogen or $C_1$-$C_{14}$-alkyl;

R is hydrogen, $C_1$-$C_{20}$-alkyl, $C_3$-$C_5$-alkenyl; $C_7$-$C_{12}$-aralkyl; CH—$CHR_6$—OH, wherein $R_6$ is hydrogen, methyl, or phenyl; —$CH_2CH_2CN$; —$CH_2$—$CH_2$—$COOC_{1-2}$alkyl; or

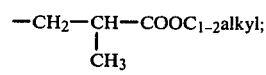

$R_1$ and $R_2$ independently of one another are $C_1$-$C_6$-alkyl, or $R_1$ and $R_2$ together with the ring carbon atom to which they are attached form $C_1$-$C_7$-cycloalkyl; and X is hydrogen.

2. The compound of claim 1, wherein
R is hydrogen or methyl;
$R_1$ and $R_2$ are each methyl; and
Z is methyl.

3. The compound of claim 1 wherein
$R_3$ is hydrogen, $C_1$-$C_8$-alkyl or cyclohexyl.

4. The compound of claim 1, wherein Z is H or methyl.

5. A process for the production of the compound of claim 1, comprising reacting a compound of the formula

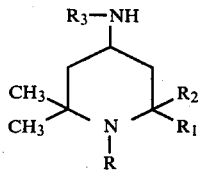

with (a) cyanic acid and then (b) formaldehyde to react each NH group not attached to the ring with cyanic acid to form first a —N—CO—$NH_2$— group and subsequently an —N—CO—NH—$CH_2OH$ group or (c) additionally etherifying the —N—CO—NH—$CH_2OH$ group with an alcohol of the formula ZOH in acid medium.

* * * * *

UNITED STATES PATENT AND TRADEMARK OFFICE
CERTIFICATE OF CORRECTION

PATENT NO. : 4,223,147

DATED : September 16, 1980

INVENTOR(S) : Harald Oertel; Paul Uhrhan; Reinhard Lantzsch; Ernst Roos; Hans Schröer, and Dieter Arlt It is certified that error appears in the above—identified patent and that said Letters Patent is hereby corrected as shown below:

Column 2, between lines 32 and 34, delete " a) -N-E with $R_3$ above N, "

Column 2, lines 40, 41, 42 should read as follows:

-- (a) $-\overset{R_3}{\underset{}{N}}- E -,$ (b) $- O - E$ or (c) $- CO - NH - NH -;$ --

UNITED STATES PATENT AND TRADEMARK OFFICE
CERTIFICATE OF CORRECTION

PATENT NO. : 4,223,147

DATED : September 16, 1980

INVENTOR(S) : Harald Oertel; Paul Uhrhan; Reinhard Lantzsch; Ernst Roos; Hans Schroer, and Dieter Arlt It is certified that error appears in the above—identified patent and that said Letters Patent is hereby corrected as shown below:

Column 4, the formula on lines 35, 36, and 37 should read

-- 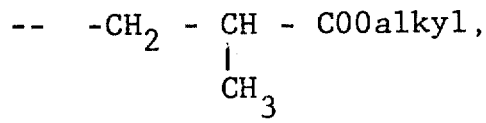 --

Column 4, line 39, delete "COOalkyl,"

Column 15, delete lines 50, 51, 53, and 54, and substitute the following therefor:

-- - A - represents a) $-\overset{3'}{N} - E -$, b) $- O - E -$ or c) $- CO - NH - NH - $ ; --

UNITED STATES PATENT AND TRADEMARK OFFICE
CERTIFICATE OF CORRECTION

PATENT NO. : 4,223,147

DATED : September 16, 1980

INVENTOR(S) : Harald Oertel, Paul Uhrhan; Reinhard Lantzsch; Ernst Roos, Hans Schroer and Dieter Arlt It is certified that error appears in the above—identified patent and that said Letters Patent is hereby corrected as shown below:

Column 26, line 38, delete "N,N',N"-tris-2,2,6,6-tetramethyl-piperidin-B  4-yl-"

and substitute the following therefor:

--N,N',N"-tris-2,2,6,6-tetramethylpiperidin-4-yl- --

Column 33, line 61, delete "methanyl" and substitute --methyl--.

Column 34, line 11, delete "processed" and substitute --processes--.

Column 41, line 17, change "agt" to --at--

UNITED STATES PATENT AND TRADEMARK OFFICE
CERTIFICATE OF CORRECTION

PATENT NO. : 4,223,147

DATED : September 16, 1980

INVENTOR(S) : Harald Oertel, Paul Uhrhan, Reinhard Lantzsch, Ernst Roos, Hans Schroer and Dieter Arlt It is certified that error appears in the above—identified patent and that said Letters Patent is hereby corrected as shown below:

Column 42, in Table 2, delete the long bracket between the last two columns and substitute in lieu thereof --)
)
)
)
)
)
)
)
)
)
)
)--

Column 42, line 15, delete horizontal line drawn across the column.

Column 42, line 19, delete the horizontal line drawn across the column.

UNITED STATES PATENT AND TRADEMARK OFFICE
CERTIFICATE OF CORRECTION

PATENT NO. : 4,223,147

DATED : September 16, 1980

INVENTOR(S) : Harald Oertel, Paul Uhrhan, Reinhard Lantzsch, Ernst Roos, Hans Schroer and Dieter Arlt It is certified that error appears in the above—identified patent and that said Letters Patent is hereby corrected as shown below:

Column 42, lines 16 to 19, "(g)" and the ensuing text as wel as "(k)" and the ensuing text should be of the same type as "(a)" and "(d)" on lines 12 and 13, and lined up directly under "(a)" and "(d)" in the manner that "(a)","(d)", "(g)" and "(k)" are set up on lines 24 to 27.

Column 43, in the footnote "(x)" in Table 3, "sill" should be --still--.

Signed and Sealed this

Tenth Day of February 1981

[SEAL]

Attest:

RENE D. TEGTMEYER

Attesting Officer     Acting Commissioner of Patents and Trademarks